United States Patent
Burdorff et al.

(10) Patent No.: US 8,460,207 B2
(45) Date of Patent: *Jun. 11, 2013

(54) SURGICAL BIOPSY SYSTEM WITH REMOTE CONTROL FOR SELECTING AN OPERATIONAL MODE

(75) Inventors: Mark A. Burdorff, Loveland, OH (US); John A. Hibner, Mason, OH (US); Dan F. Dlugos, West Chester, OH (US); Jon D. Buzzard, Milford, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 158 days.

This patent is subject to a terminal disclaimer.

(21) Appl. No.: 13/040,788

(22) Filed: Mar. 4, 2011

(65) Prior Publication Data

US 2011/0160610 A1   Jun. 30, 2011

Related U.S. Application Data

(60) Continuation of application No. 10/842,314, filed on May 7, 2004, now Pat. No. 7,914,464, which is a division of application No. 10/174,032, filed on Jun. 18, 2002, now Pat. No. 6,752,768, which is a continuation of application No. 09/466,491, filed on Dec. 17, 1999, now Pat. No. 6,428,487.

(51) Int. Cl.
*A61B 10/00*   (2006.01)

(52) U.S. Cl.
USPC .................................................. 600/568

(58) Field of Classification Search
USPC ........... 600/564–568, 562; 606/180, 185, 606/159, 170, 171, 167, 168, 1, 13, 27, 45, 606/34; 604/118, 152, 67, 22; 128/203.12; 434/262; 178/18.01, 18.02; 715/700, 764, 715/810, 853; 345/173, 179

See application file for complete search history.

(56) References Cited

U.S. PATENT DOCUMENTS

| | | |
|---|---|---|
| 33,258 A | 9/1861 | Miller |
| 3,732,858 A | 5/1973 | Banko |

(Continued)

FOREIGN PATENT DOCUMENTS

| | | |
|---|---|---|
| EP | 0 378692 | 7/1990 |
| GB | 2 208 601 | 10/1979 |

(Continued)

OTHER PUBLICATIONS

U.S. Appl. No. 09/178,075, filed Oct. 23, 1998, Privitera.

(Continued)

*Primary Examiner* — Brian Szmal
(74) *Attorney, Agent, or Firm* — Frost Brown Todd LLC

(57) ABSTRACT

A surgical biopsy system is provided for removing at least one tissue sample from a surgical patient. The surgical biopsy system comprises an elongated, hollow piercer and a cutter rotatably and axially positionable relative to the piercer. The piercer has a lateral port for receiving the tissue sample into the piercer. The surgical biopsy system further comprises a power transmission source operatively connected to the cutter for rotating and translating the cutter, a control unit, and a display mounted in a display frame for showing an operator a plurality of operational modes of the surgical biopsy system. The surgical biopsy system further comprises at least one control button operatively connected to the control unit by a circuit and remotely located from the control unit. The operator may actuate the control button(s) to select any one of the operational modes and the selected operational mode is visually identifiable on the display.

20 Claims, 18 Drawing Sheets

U.S. PATENT DOCUMENTS

| | | | |
|---|---|---|---|
| 3,734,099 | A | 5/1973 | Bender et al. |
| 3,945,375 | A | 3/1976 | Banko |
| 3,996,935 | A | 12/1976 | Banko |
| 4,203,444 | A | 5/1980 | Bonnell et al. |
| 4,320,761 | A | 3/1982 | Haddad |
| 4,517,977 | A | 5/1985 | Frost |
| 4,919,146 | A | 4/1990 | Rhinehart et al. |
| 4,995,877 | A | 2/1991 | Ams et al. |
| 5,112,299 | A | 5/1992 | Pascaloff |
| 5,133,359 | A | 7/1992 | Kedem |
| 5,197,484 | A | 3/1993 | Kornberg et al. |
| 5,217,478 | A | 6/1993 | Rexroth |
| 5,290,303 | A | 3/1994 | Pingleton et al. |
| 5,353,804 | A | 10/1994 | Kornbery et al. |
| 5,415,169 | A | 5/1995 | Siczek et al. |
| 5,431,645 | A | 7/1995 | Smith et al. |
| 5,455,766 | A | 10/1995 | Scheller et al. |
| 5,526,822 | A | 6/1996 | Burbank et al. |
| 5,543,695 | A | 8/1996 | Culp et al. |
| 5,602,449 | A | 2/1997 | Krause et al. |
| 5,643,304 | A | 7/1997 | Schechter et al. |
| 5,649,547 | A | 7/1997 | Ritchert et al. |
| 5,685,838 | A | 11/1997 | Peters et al. |
| 5,685,840 | A | 11/1997 | Schechter et al. |
| 5,689,159 | A | 11/1997 | Culp et al. |
| 5,769,086 | A | 6/1998 | Ritchart et al. |
| 5,775,333 | A | 7/1998 | Burbank et al. |
| 5,791,908 | A | 8/1998 | Gillio |
| 5,804,936 | A | 9/1998 | Brodsky et al. |
| 5,830,219 | A | 11/1998 | Bird et al. |
| 5,849,023 | A | 12/1998 | Mericle |
| 5,871,454 | A | 2/1999 | Majlessi |
| 5,891,157 | A | 4/1999 | Day et al. |
| 5,910,139 | A | 6/1999 | Cochran et al. |
| 5,944,673 | A | 8/1999 | Gregoire et al. |
| 5,976,164 | A | 11/1999 | Bencini et al. |
| 6,017,316 | A | 1/2000 | Ritchart et al. |
| 6,019,733 | A | 2/2000 | Farascioni |
| 6,086,544 | A | 7/2000 | Hibner et al. |
| 6,106,512 | A | 8/2000 | Cochran et al. |
| 6,120,462 | A | 9/2000 | Hibner et al. |
| 6,162,187 | A | 12/2000 | Buzzard et al. |
| 6,245,084 | B1 | 6/2001 | Mark et al. |
| 6,273,862 | B1 | 8/2001 | Privitera et al. |
| 6,340,979 | B1 | 1/2002 | Beaton et al. |
| 6,428,487 | B1 | 8/2002 | Burdorff et al. |
| 6,432,065 | B1 * | 8/2002 | Burdorff et al. .............. 600/566 |
| 6,602,227 | B1 | 8/2003 | Cimino et al. |
| 6,745,764 | B2 | 6/2004 | Hickle |
| 6,752,768 | B2 | 6/2004 | Burdorff et al. |
| 6,945,954 | B2 | 9/2005 | Hochman et al. |
| 7,914,464 | B2 * | 3/2011 | Burdorff et al. .............. 600/568 |
| 2001/0047183 | A1 | 11/2001 | Privitera et al. |
| 2004/0034280 | A1 | 2/2004 | Privitera et al. |
| 2004/0034340 | A1 | 2/2004 | Biscup |

FOREIGN PATENT DOCUMENTS

| | | |
|---|---|---|
| WO | WO 93/14707 | 8/1993 |
| WO | WO 95/08959 | 4/1995 |
| WO | WO 9525465 | 9/1995 |
| WO | WO 98/06338 | 2/1998 |
| WO | WO 98/25556 | 6/1998 |

OTHER PUBLICATIONS

Burbank, F., "Stereotactic Breast Biopsy of Atypical Ductal Hyperplasia and Ductal Carcinoma in Situ Lesions: Improved Accuracy with Directional, Vacuum-Assisted Biopsy," Radiology, 202 (1997) pp. 843-847.

Burbank, F., "Stereotactic Breast Biopsy: Its History, Its Present, and Its Future," The American Surgeon, vol. 62 (1996) pp. 128-150.

Ethicon Endo-Surgery, Inc., "Defendants Hologic, Inc.'s and Suros Surgical Systems, Inc.'s Preliminary Invalidity Contentions," Civil Action No. 07-00834 (Apr. 25, 2008) pp. 1-9.

Ethicon Endo-Surgery, Inc., "Defendants Hologic, Inc.'s and Suros Surgical Systems, Inc.'s Supplemental Preliminary Invalidity Contentions," Civil Action No. 07-00834 (Jul. 25, 2008) pp. 1-58.

"Mammotom® Biopsy System User Guide for the Fischer Imaging Stereotactic Prone Table," Biopsys Medical, Inc. (1997) pp. 1-209.

"Mammotom® Biopsy System User Guide for the Lorad Stereotactic Prone Table," Biopsys Medical, Inc. (1997) pp. 1-23.

"Mammotom® Ultrasound Multi-Probe Probe and Power Driver Instructions for Use," Biopsys Medical, Inc. (1997) pp. 1-3.

Office Action dated Apr. 10, 2006 for U.S. Appl. No. 10/842,314.

Parker, S.H. et al., "A Practical Approach to Minimally Invasive Breast Biopsy," Radiology, vol. 200 (1996) pp. 11-20.

Parker, S.H. et al., "Critical Pathways in Percutaneous Breast Intervention," RadioGraphics, vol. 15(4) (1995) 946-950.

Parker, S.H., "Evolution of the Standard Stereotactic Biopsy Technique," 27$^{th}$ National Conference on Breast Cancer (1996) pp. 114-115.

Parker, S.H. et al., "Performing a Breast Biopsy with a Directional, Vacuum-assisted Biopsy Instrument," RadioGraphics, vol. 17(5)(1997) pp. 1233-1252.

* cited by examiner

SURGICAL BIOPSY SYSTEM WITH REMOTE CONTROL FOR SELECTING AN OPERATIONAL MODE

This application is a continuation of U.S. patent application Ser. No. 10/842,314, filed on May 7, 2004; which is a divisional of U.S. patent application Ser. No. 10/174,032, filed on Jun. 18, 2002, now U.S. Pat. No. 6,752,768, issued Jun. 22, 2004; which is a continuation of U.S. patent application Ser. No. 09/466,491, filed Dec. 17, 1999, now U.S. Pat. No. 6,428,487, issued Aug. 6, 2002, all of which are incorporated by reference herein.

Subject matter in this application is related to subject matter in the following co-pending U.S. patent applications: Ser. No. 09/178,075, filed on Oct. 23, 1998, now abandoned; Ser. No. 09/282,142, filed on Mar. 31, 1999, now U.S. Pat. No. 6,086,544, issued Jul. 11, 2000; Ser. No. 09/282,140, filed on Mar. 31, 1999, now U.S. Pat. No. 6,120,462, issued Sep. 19, 2000; and Ser. No. 09/365,619, filed on Aug. 2, 1999, now U.S. Pat. No. 6,162,187, issued Dec. 19, 2000. Subject matter in this application is further related to subject matter in U.S. patent application Ser. No. 09/466,391, filed on Dec. 17, 1999, now U.S. Pat. No. 6,432,065, issued Aug. 13, 2002, which is hereby incorporated by reference.

FIELD OF THE INVENTION

The present invention relates, in general, to remotely controlled surgical instruments, and more particularly, to a remotely controlled, surgical biopsy instrument including an apparatus for remotely selecting a particular mode of operation.

BACKGROUND OF THE INVENTION

The diagnosis and treatment of patients with cancerous tumors, pre-malignant conditions, and other disorders has long been an area of intense investigation. Non-invasive methods for examining tissue include: palpation, X-ray imaging, magnetic resonance imaging (MRI), computed tomography (CT), and ultrasound imaging. When a physician suspects that tissue may contain cancerous cells, a biopsy may be done using either an open procedure or a percutaneous procedure. For an open procedure, a scalpel is used to create a large incision to provide direct visualization of and access to the tissue mass of interest. The entire mass (excisional biopsy) or a part of the mass (incisional biopsy) may then be removed. In percutaneous biopsy procedures, a needle-shaped instrument is inserted through a small incision to access the tissue mass of interest and obtain a tissue sample for later examination and analysis.

Aspiration and core sampling are two percutaneous methods for obtaining tissue from within the body. In an aspiration procedure, tissue is fragmented into pieces and drawn through a fine needle in a fluid medium. The aspiration method is less intrusive than most other sampling techniques, however, it has limited application since the structure of tissue excised by aspiration is destroyed, leaving only individual cells for analysis. In core biopsy, a core or fragment of tissue is obtained in a manner which preserves both the individual cell and the tissue structure for histological examination. The type of biopsy used depends on various factors, no single procedure is ideal for all cases.

Ethicon Endo-Surgery, Inc., Cincinnati, Ohio currently markets a core sampling biopsy instrument under the MAMMOTOME trademark. The MAMMOTOME biopsy instrument is normally mounted on a movable mechanical arm attached to an X-ray stereotactic imaging device. The MAMMOTOME biopsy instrument is adapted to obtain multiple tissue samples from a patient with only one percutaneous insertion of a piercing element or piercer into the patient's breast. An operator uses the MAMMOTOME biopsy instrument to "actively" capture (using a vacuum) tissue prior to severing it from surrounding tissue. Tissue is drawn into a lateral port at the distal end of the piercer by a remotely actuated vacuum system. Once the tissue is in the lateral port, a cutter is rotated and advanced through a lumen of the piercer past the lateral port. As the cutter advances past the lateral port opening, it severs the tissue in the port from the surrounding tissue. When the cutter retracts it pulls the tissue with it and deposits the tissue sample outside of the patient's body. The cutter is rotated using a motor, but the operator manually advances and retracts the cutter manually by moving a knob mounted on the outside of the instrument. The operator has tactile and audible feedback to determine whether the cutter is effectively cutting tissue. An alternative instrument wherein the cutter is advanced and retracted manually is illustrated and described in U.S. patent application Ser. Nos. 09/282,142 and 09/282,140.

Related patent applications, Ser. No. 09/282,142 and Ser. No. 09/282,140 also describe a control method and apparatus for an automatic, core sampling biopsy device. In one embodiment, cutter translation and rotation are driven by motors separate from the handpiece and operatively connected by a control cord and a pair of flexible, rotatable shafts. The operator steers the piercer of the handpiece towards a suspect tissue mass visualized using, for example, a handheld ultrasound-imaging device. Buttons on the handpiece generally enable the operator to advance or retract the cutter to obtain a tissue sample, or to activate the vacuum to draw in tissue.

A common problem encountered by operators when using some types of automatic, powered surgical devices is the need for the operator to move back and forth between the patient and a control unit physically separated from the patient. Reaching out to change a setting or mode could require that the operator move from a sterile, surgical field to a non-sterile area, and back again. In a surgical instrument which has a plurality of operational modes, the operator selects a particular mode and the associated control unit automatically operates the device through selected portions of the surgical procedure. For breast biopsy procedures using handheld biopsy devices such those described above, the operator may also need to use both hands during the procedure, one to hold the instrument and one to for example, palpate tissue or to use a handheld ultrasonic imaging device to locate a possible lesion As an example, either immediately before or after the piercer is inserted into the suspected tissue, the operator enables a mode of operation which may be referred to as a Sampling Mode of operation wherein the cutter is automatically advanced to collect a tissue sample. It is highly undesirable at this point for the operator to free one hand and to reach over to the control unit to actuate a control in order to select and enable the Sampling Mode of operation. Since a surgical biopsy device may have a plurality of operational modes, it is desirable to be able to "scroll" among possible operational mode choices, make a selection, and enable the selected mode, without releasing the handpiece or leaving the surgical field. The operational mode choices, or "menu", may be viewed, for example, on a display provided with the surgical biopsy device.

Numerous types of surgical biopsy systems having various types of control devices are known in the art. U.S. Pat. No. 5,769,086 discloses an automatic control system for a vacuum-assisted automatic core biopsy device. The system in U.S. Pat. No. 5,769,086 may be used with an imaging device having a monitor for viewing still images of tissue. A hand-operated cursor (mouse) is used to click on portions of the tissue image viewed on the monitor to automatically direct a needle of the biopsy device to the tissue. U.S. Pat. No. 5,830,219 discloses a rotary cutting surgical instrument mounted on the needle guiding stage of a stereotactic mammography biopsy system. The system in U.S. Pat. No. 5,830,219 is provided with a controlling means having motor controls. Neither Ritchart nor Bird, however, disclose a control adapted for remotely selecting and/or enabling an operational mode from a menu shown on a display without leaving the surgical field.

It would, therefore, be advantageous to design a surgical biopsy system having at least one remotely located (from the control unit) control button for selecting and enabling an operational mode. It would further be advantageous to design a surgical biopsy system wherein an operator, without leaving the surgical field, may actuate the remotely located control button(s) while performing the biopsy procedure. It would further be advantageous to design a surgical biopsy system having a display for showing the operator the available operational modes, so that the operator may scroll through the operational modes using the remotely located control button(s), and enable a selected operational mode by actuating one or more of the remotely located control buttons.

SUMMARY OF THE INVENTION

The present invention is directed to a surgical biopsy system for removing at least one tissue sample from a surgical patient. The surgical biopsy system comprises an elongated, hollow piercer and a cutter rotatably and axially positionable relative to the piercer. The piercer has a lateral port for receiving the tissue sample. The surgical biopsy system further comprises a power transmission source operatively connected to the cutter for rotating and translating the cutter. The surgical biopsy system further comprises a control unit and a display mounted in a display frame for showing an operator a plurality of operational modes of the surgical biopsy system. The surgical biopsy system further comprises at least one control button operationally connected to the control unit by a circuit and remotely located from the control unit. The operator actuates the control button to select any one of the operational modes, whereupon the selected operational mode becomes visually identifiable on the display. The operator may also actuate the control button to enable the selected operational mode of the surgical biopsy system.

In one embodiment of the present invention, the surgical biopsy system also has a handpiece comprising a holster operationally connected to the control unit, and a probe assembly detachably connected to the holster. The piercer extends distally from the probe assembly. The control button is operationally mounted on the handpiece so that the operator can select and enable an operational mode without releasing the handpiece.

In another embodiment of the present invention, the surgical biopsy system has a remote control device operatively connected to and remotely located from the control unit. At least one control button is operationally mounted on the remote control device. The operator actuates the control button to select an operational mode of the surgical system. The control button is used to enable the selected operational mode. The remote control device operatively connects to the control unit by a remote control cord. In a further embodiment, the control button on the remote control device is a foot operable control switch.

In another embodiment of the present invention, a fluid collection system is provided to assist in drawing tissue into the port, transferring the tissue sample from the patient, removing fluid from the patient, and injecting fluid into the patient. In addition, translation in the distal direction of the cutter is manually controllable by a forward button, translation in the proximal direction of the cutter is manually controllable by a reverse button, and actuation of the fluid collection system is manually controllable by a vacuum button. At least one of the forward, reverse, and vacuum buttons is used to select and enable an operational mode from a plurality of operational modes shown on a display.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
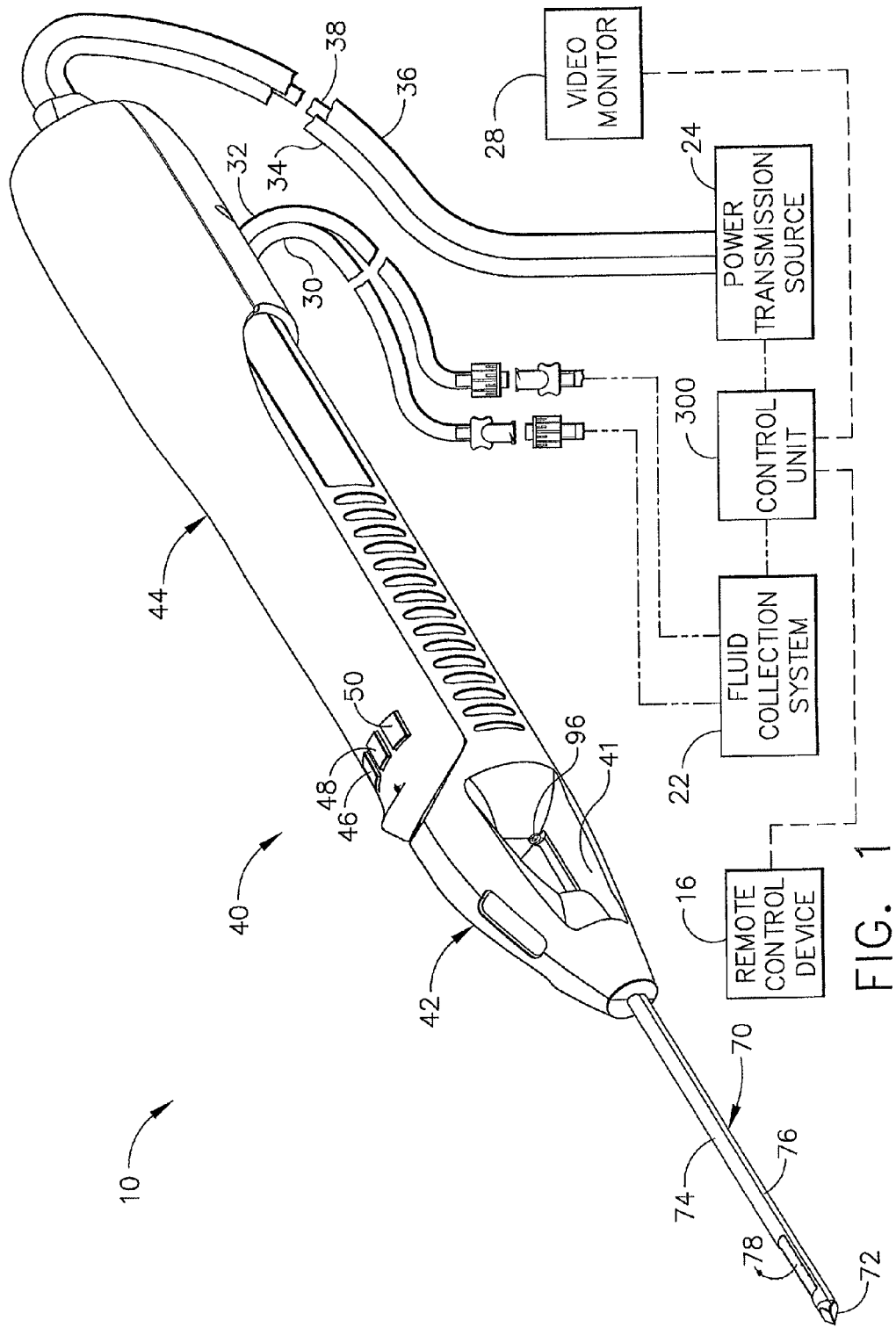
FIG. 1 is an isometric view of a surgical biopsy system for the collection of at least one core tissue sample from a surgical patient.

FIG. 1 shows a surgical biopsy system 10 comprising a handpiece 40, a fluid collection system 22, a control unit 300, a power transmission source 24, a video monitor 28 and a remote control 16. Detailed descriptions of surgical biopsy system 10 are contained in U.S. patent Ser. No. 09/282,140 filed Mar. 31, 1999, which is hereby incorporated herein by reference. Handpiece 40 comprises a holster 44 operatively and removeably attached to a probe assembly 42. Handpiece 40 is lightweight, ergonomically shaped, and hand manipulatable. Probe assembly 42 includes an elongated piercer 70 having a piercer tip 72 for penetrating soft tissue of a surgical patient. Piercer 70 comprises a piercer tube 74 and a vacuum chamber tube 76. Vacuum chamber tube 76 of piercer 70 may be fluidly connected, automatically or manually, to fluid collection system 22 by a lateral vacuum line 30. Similarly, axial vacuum line 32 may be fluidly connected, automatically or manually, to fluid collection system 22. Lateral and axial vacuum lines, 30 and 32, are detachably connected to fluid collection system 22. Holster 44 is operatively connected to control unit 300 by a control cord 38 and to power transmission source 24 by a translation shaft 34, and a rotation shaft 36. Shafts 34 and 36 are preferably flexible so that the operator may easily manipulate handpiece 40 with one hand.

Still referring to FIG. 1, holster 44 further comprises: a forward button 46 which may be used to move cutter 96 distally through piercer tube 74 and sever tissue collected in port 78; a reverse button 48 which may be used to move cutter 96 proximally through piercer tube 74 and thereby moving the tissue sample in port 78 to a collection surface 41; and a vacuum button 50 which may be used to open or close vacuum lines 30 and 32, thereby generally for administering and/or removing fluids from handpiece 40.

An operator may use surgical biopsy system 10 with a handheld, ultrasonic imaging device for visualizing the removal of suspected tissue from a patient. The imaging device provides a real-time image of lesions, microcalcifications, and high-density masses within the breast tissue of the patient. The operator may view a suspected tissue mass while guiding piercer tip 72 of handpiece 40 to a location adjacent to the suspected tissue in order to obtain a core tissue sample. The surgical biopsy system 10 may also be mounted in a holder of a mechanical arm or the like, and used with other imaging devices such as stereotactic X-ray.

Figure 2:
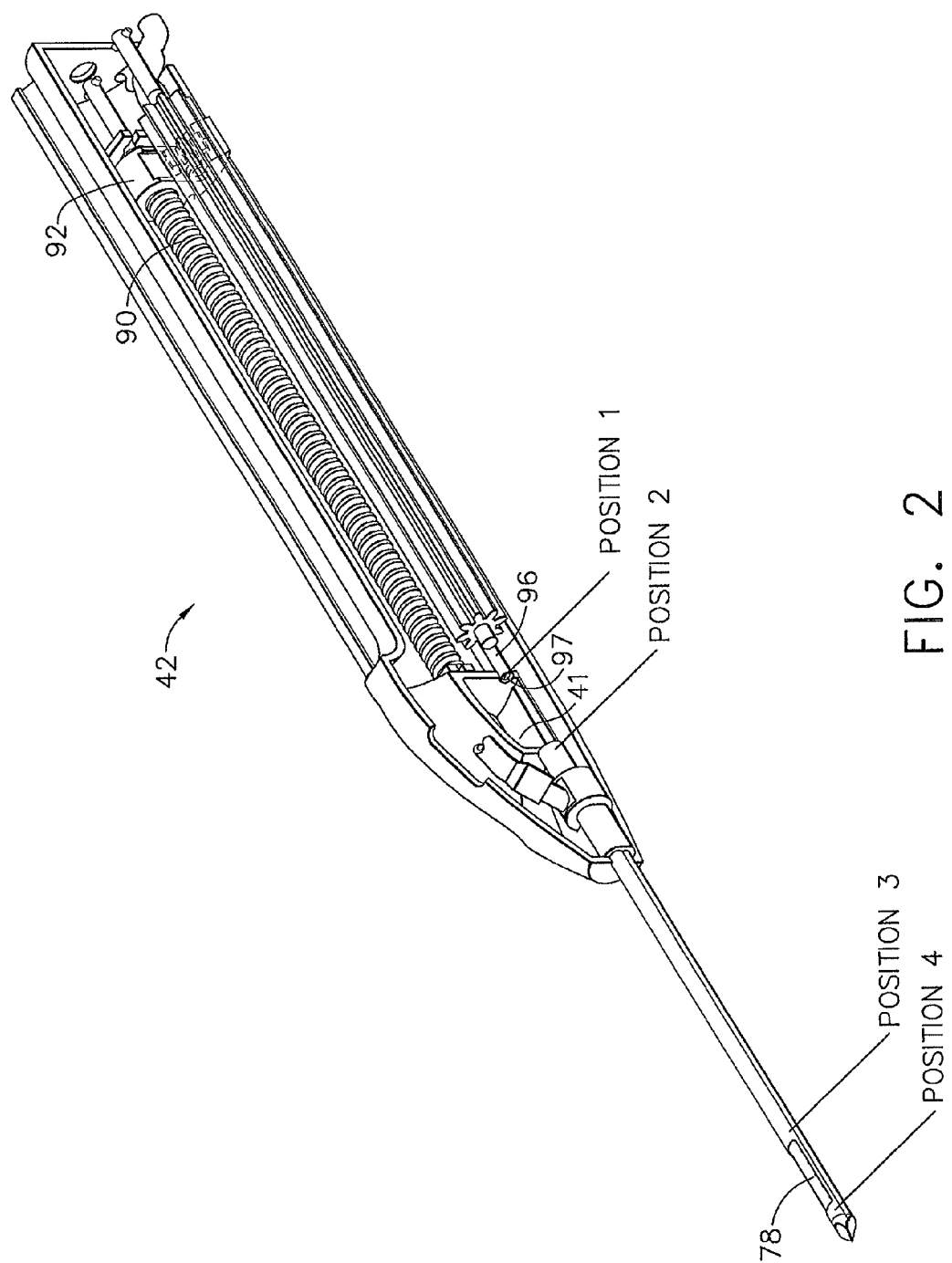
FIG. 2 is an isometric view of a probe assembly of the surgical biopsy system of FIG. 1 with the left handle shell removed.

FIG. 2 is an isometric view of probe assembly 42 with a left handle shell removed to reveal a cutter 96 which has a cutter blade 97. Cutter 96 is an elongated, metal tube that translates in either direction between a fully retracted position (where cutter blade 97 is immediately proximal to collection surface 41) and a fully deployed position (where cutter blade 97 is immediately distal to port 78). During portions of cutter translation, cutter 96 is rotated at an appropriate speed for severing tissue from a patient. Cutter 96 is attached to a carriage 92, which is driven by a lead screw 90, which in turn is driven by translation shaft 34 (FIG. 1). For the embodiment shown in FIG. 2, one revolution of lead screw 90 causes cutter 96 to translate 0.100 inches. There are key intermediate positions along the translation length of cutter 96, When cutter blade 97 of cutter 96 reaches each of these positions, and depending upon the operational mode the system is in, important adjustments to either the cutter rotational speed (sometimes called rotation speed) or the cutter translational speed (sometimes called translation speed), or both, are made automatically. Fluid collection system 22 may also be engaged according to the position of cutter 96, which includes cutter blade 97, position and depending on operational mode being used. For the embodiment of surgical biopsy system 10 described herein, there are four positions along the length of the cutter translation. At these positions, signals are sent to control unit 300 and used to make appropriate adjustments to cutter rotational speed and/or cutter translational speed. As shown in FIG. 2, the four cutter positions are the following: a first position, Position 1, where cutter blade 97 is immediately proximal to tissue sampling area 41; a second position, Position 2, where cutter blade 97 is immediately distal to tissue sampling area 41; a third position, Position 3, where cutter blade 97 is immediately proximal to port 78; and a fourth position, Position 4, where cutter blade 97 is immediately distal to port 78. The four cutter positions are given by way of example although numerous other cutter positions may be used in the present invention for automatically signaling adjustments to cutter rotational speed and/or translational speed, and for engaging fluid collection system 22. For example, a fifth position of cutter 96 may be at a location about 2 mm proximal to port 78. The rotation, of the cutter 96 may then be accelerated to the appropriate speed (1100 rpm, for example) slightly before cutter 96 encounters tissue prolapsed into port 78. Likewise, a sixth position of cutter 96 may be at a location about 2 mm distal to port 78 so that cutter 96 is decelerated after it has traversed the entire length of the port 78.

Figure 3:
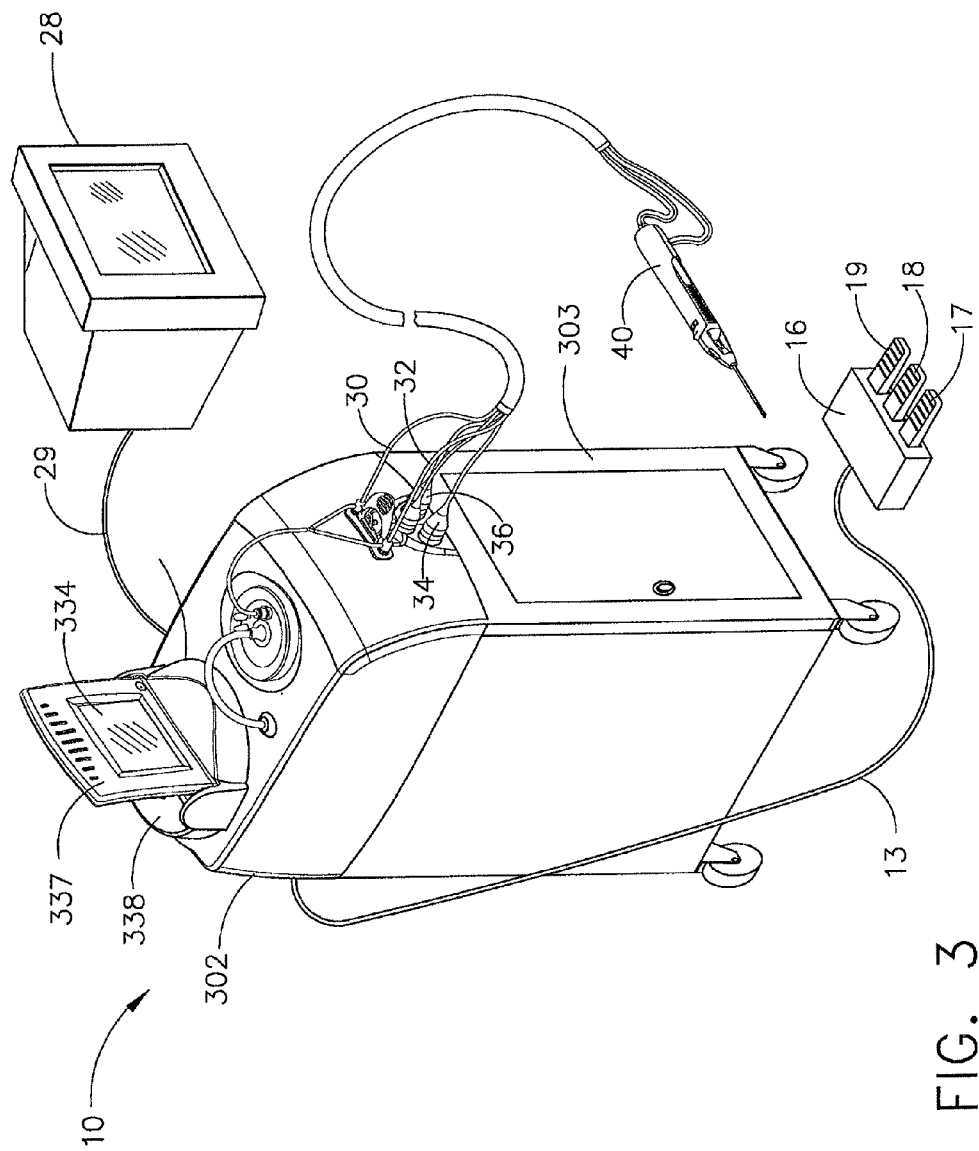
FIG. 3 is an isometric view of the surgical biopsy system of FIG. 1, showing a display pivotally and tiltably mounted on a control console.

FIG. 3 shows surgical biopsy system 10 having a remote control 16 (also called a remote control device) operatively connected to a console 302 (containing control unit 300) by a remote control cord 13. Console 302 of FIG. 3 is shown to be mounted on a portable, wheeled unit having a storage space 303 that may be used, for example, for storing surgical supplies and equipment. Remote control 16 comprises a first remote switch 17, a second remote switch 18, and a third remote switch 19. Remote switches 17, 18 and 19 perform the same functions as buttons 46, 48, and 50 on handpiece 40 (FIG. 1). Remote control 16, as shown in the embodiment of FIG. 3, may be foot operable. A suitable example of a foot operable, remote control 16 is TREADLITE, a footswitch sold under the trademark and available from Linemaster, Inc. and part number T-91-SWNO. Those skilled in the art will appreciate that remote control 16 may have other embodiments, including those adapted for hand operation or other means of actuation. Wireless means of interfacing with control unit 300 are also available and could be incorporated into the present invention.

FIG. 3 also shows video monitor 28 operatively connected to console 302 (containing control unit 300) by a video cord 29. A video output connection (not shown) is provided on the back of console 302 and operatively connected to control unit 300. Video monitor 28 displays the image shown on a display 334 mounted on console 302, and enables the operator, assistant, patient, or others to view the display image more easily. Video monitor 28, in addition to facilitating the surgical procedure, may be used as a teaching tool for other users. The video image supplied from control unit 300 may also be transmitted without wires to other locations, or may be recorded on conventional video recording devices for later viewing. In the embodiment shown in FIG. 3, a display frame 337 supports display 334 and is tiltably attached to a turntable 338. Turntable 338 is rotatably attached to the top of console 302. Display 334 is not restricted to the location shown in FIG. 3. For example, a smaller version of display 334 may be mounted on handpiece 40 or removeably attached to the surgical table on which the patient is lying.

Figure 4:
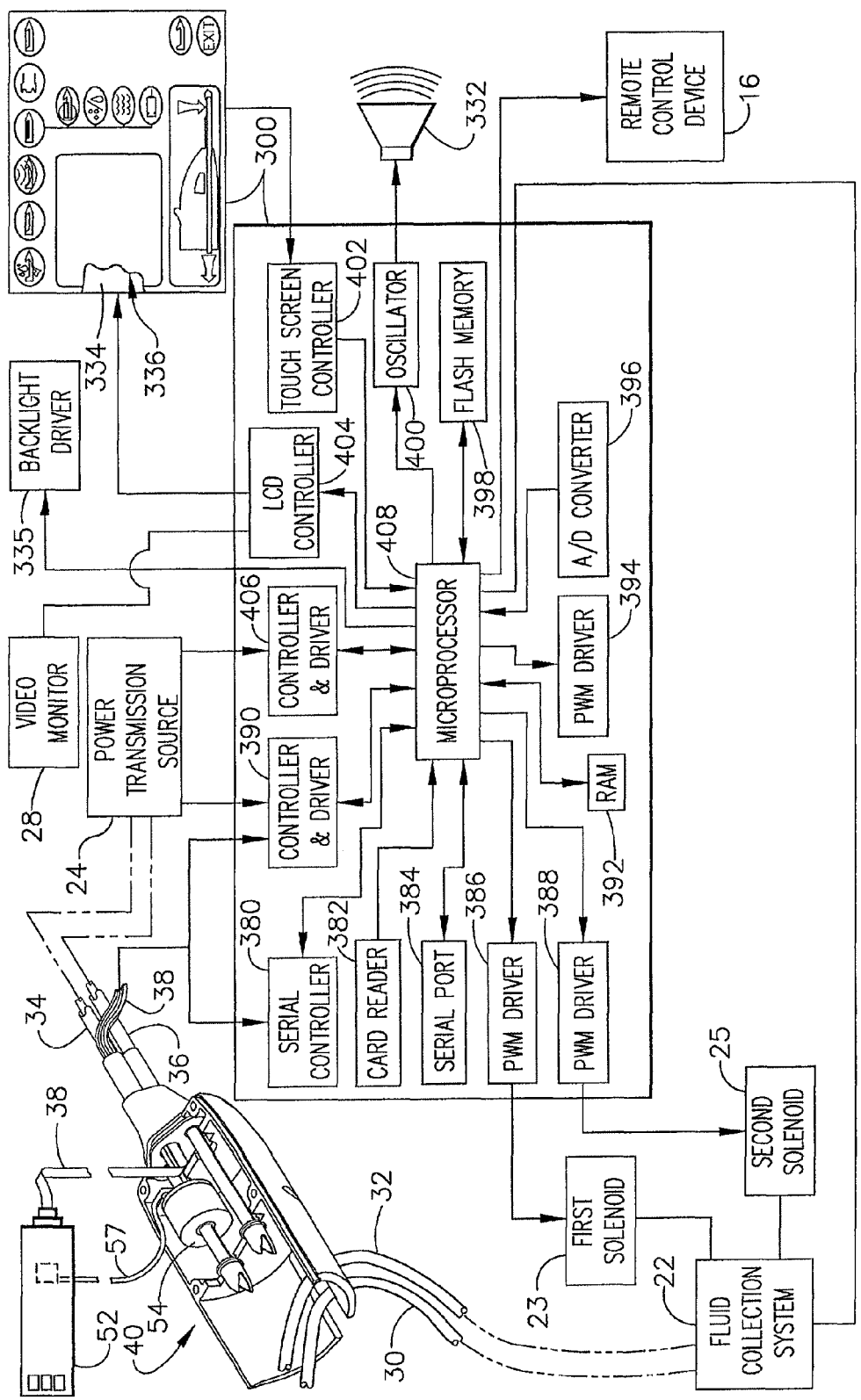
FIG. 4 is a schematic diagram representation of a control unit interfaced with the surgical biopsy system of FIG. 1.

FIG. 4 is a representation of surgical biopsy system 10 of FIG. 1 illustrating the interface of the electro-mechanical components to control unit 300. In the embodiment of the surgical biopsy system 10 shown in FIG. 3, all of the components of FIG. 4 are contained in portable console 302. The operator may therefore move surgical biopsy system 10 easily from one room to another, such as in a physician's office or clinic. For each new patient, a new sterile probe assembly 42 may be operatively connected to reusable holster 44. Handpiece 40 (probe assembly 42 and holster 44 together) may be mounted, for example, to an X-ray, stereotactic table already in the room, or handheld and used in combination with a handheld ultrasonic imaging device.

FIG. 4 illustrates the connection of handpiece 40 and power transmission source 24 to control unit 300. Power transmission source 24 comprises a rotation motor and a translation motor (not shown). A rotation sensor 54 is shown mounted in handpiece 40 and operatively connected to switchboard 52 by a conductor 57. Rotation sensor 54 counts the revolutions of lead screw 90 (see FIG. 2), providing a signal to control unit 300 and representing the actual position of cutter 96 as it translates between positions 1 and 4. It is therefore possible for control unit 300 to compare the actual axial position of cutter 96 to the position commanded by control unit 300. In one embodiment, rotation sensor 54 provides a signal of 1200 "counts" per revolution to control unit 300. During the translation of cutter 96, control unit 300 sums the total number of counts received from rotation sensor 54. Due to mechanical losses (shaft twisting, etc.) the total number of counts for rotation sensor 54 is typically less than the total number of counts commanded by control unit 300. When the difference of the actual and commanded positions is significant enough to represent a substantial cutter axial position error, the operator is alerted and may halt the procedure. A cutter translation position differential, PD, represents a maximal, allowable differential between the summed counts of the rotation sensor 54 in handpiece 40 and the commanded position in terms of counts. In one embodiment of the present invention, control unit 300 is programmed to alert the operator when PD is more than 1000 counts, corresponding to a translation position error of 0.083 inches (1000/1200 of one revolution of lead screw 90, or 0.83 times 0.100 inches).

Control unit 300 of FIG. 4 provides a means for either increasing cutter rotation speed or slowing cutter translation speed, or both, if cutter 96 rotation speed slows below a predetermined limit due to obstructions to cutter 96 or mechanical resistance within the system. Control unit 300 also provides a means for varying cutter translation and rotation speed in response to cutter axial position.

In FIG. 4 control unit 300 is shown to include elements such as, a display 334, a backlight driver 335, and a touchscreen 336. At the heart of control unit 300 is a microprocessor 408, which is designed to perform logic operations that may be translated into simple electromechanical actions. Display 334 prompts and informs the operator during the operation of surgical biopsy system 10. Touchscreen 336 covers display 334 for one user interface. Touchscreen 336 is electronically connected to a touchscreen controller 402 in control unit 300. A backlight (not shown) is integrally constructed within display 334 and provides illumination of display 334 when control unit 300 is powered-up. A backlight driver 335 interfaces the backlight with microprocessor 408. A suitable example of backlight driver 335 is Part Number LS520 available from Xentek, Inc.

Still referring to FIG. 4, touchscreen controller 402 allows control unit 300 to respond to the operator's touch. A LCD controller 404 is provided to interface between microprocessor 408 and display 334. LCD controller 404 reduces the burden of microprocessor 408 by efficiently controlling display parameters such as color, shading, screen update rates, and provides temporary storage for display information. A miniature annunciator 332 is provided with control unit 300 in order to provide the operator with audible feedback "beeps" upon each activation of an icon control on display 334. Annunciator 332 interfaces with microprocessor 408 by an oscillator 400 which converts the digital signal from microprocessor 408 to analog, periodic output signals, thus controlling the audio frequency of annunciator 332.

Still referring to FIG. 4, a first and a second controller and driver, 390 and 406, convert digital signals from microprocessor 408 into analog motor signals for controlling power transmission source 24 rotational direction and speed. Closed loop, digital, translation speed control of power transmission source 24 is also achieved within controller and driver 390 using feedback signals from rotation sensor 54 in handpiece 40. Handpiece 40 contains a switchboard 52 having a first circuit 212 (see FIG. 5). A serial controller 380 is electronically connected to switchboard 52 by control cord 38. Serial controller 380 coordinates information exchange across the serial communication link between switchboard 52 and microprocessor 408. An optional card reader 382 may be provided in control unit 300 for reading data from a memory card in order to facilitate future software upgrades and servicing. A serial port 384 is provided for the bi-directional data exchange in a serial transmission mode, again to facilitate future software upgrades and servicing. A first PWM (pulse width modulation) driver 386 interfaces a first solenoid 23 with microprocessor 408. First PWM driver 386 converts a digital input signal from microprocessor 408 to an analog output signal having a wave of fixed frequency and amplitude, but varying duty cycle. First PWM driver 386 outputs a 100% duty cycle frequency to move initially a first solenoid 23 in order to open lateral vacuum line 30 to the vacuum source of fluid collection system 22. Once first solenoid 23 is actuated, the duty cycle is reduced to a level that maintains solenoid position, thus minimizing power requirements. A second PWM driver 388 similarly interfaces a second solenoid 25 with microprocessor 408 to open axial vacuum line 32 to the vacuum source. A third PWM driver 394 interfaces with a pressure sensor (not shown) of fluid collection system 22 and with an A/D converter 396.

Still referring to FIG. 4, a RAM (Random Access Memory) memory device 392 is provided with microprocessor 408 for storing variable data, and inherently loses stored data when power is removed. A flash memory device 398 is provided with microprocessor 408 to store data, including the main application, program or variable data, even without power. A/D converter 396 converts voltage signals corresponding to vacuum pressure signals from fluid collection system 22 into digital signals which are transmitted to microprocessor 408, and used by microprocessor 408 to maintain a desired vacuum pressure in fluid collection system 22. Control unit 300 is provided with a conventional, 48-volt DC power supply (not shown) used in combination with standard DC-to-DC converters and electrical voltage regulators in order to supply reduced voltages to the components of control unit 300.

Figure 5:
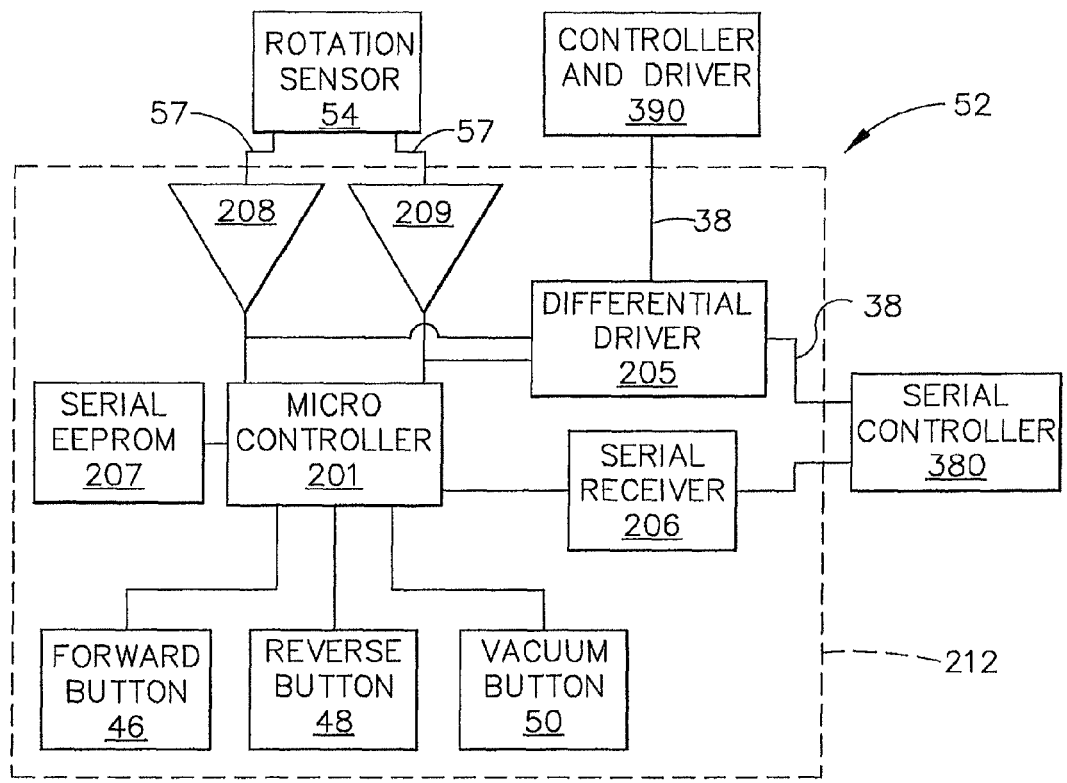
FIG. 5 is a schematic diagram of a first electronic circuit including control buttons for use with the surgical biopsy system of FIG. 1, interfacing with a portion of the control unit of FIG. 4.

FIG. 5 is a schematic representation of first circuit 212 of switchboard 52 (see FIG. 4) interfacing with rotation sensor 54 of handpiece 40, serial controller 380 of control unit 300, and controller and driver 390 of control unit 300. Rotation sensor 54 may be implemented using, for example, an encoder to count the shaft resolutions. First circuit 212 comprises a microcontroller 201 operatively connected in parallel to forward button 46, reverse button 48, and vacuum button 50. Rotation sensor 54 interfaces with microcontroller 201 and microprocessor 408 via a first comparator 208 and a second comparator 209. Comparators 208 and 209 convert sine wave peak-to-peak waveforms (from rotation sensor 54) to square wave logic level outputs, and are available as P/N LM2903 from National Semiconductor Corporation. A serial EEPROM 207 is provided to store permanent non-volatile data for reliability and is available as P/N 25C040-SN from Microchip, Inc. A serial receiver 206 interfaces serial controller 380 of control unit 300 with microcontroller 201 and provides serially formatted data for storage in non-volatile memory. Serial receiver 206 is available as P/N IC-RS-485 SN 75 LBC 179D from Texas Instrument Corp. A differential driver 205 interfaces with microcontroller 201, serial controller 380, controller and driver 390, and rotation sensor 54 to communicate serial data and rotation sensor 54 signals. Serial receiver 205 is available as P/N IC-RS-485 LTC 486CS from Texas Instrument Corp.

Figure 6:
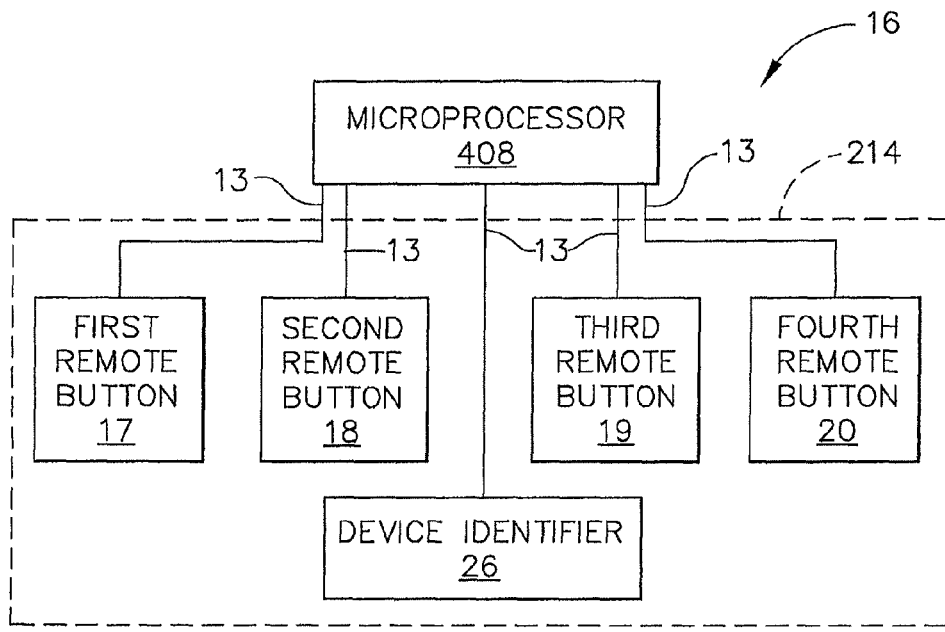
FIG. 6 is a schematic diagram of a second electronic circuit including foot operated control switches interfacing with a portion of the control unit of FIG. 4.

FIG. 6 is a schematic representation of a second circuit 214 in remote control 16 interfacing with microprocessor 408 of control unit 300. Second circuit 214 is located inside of remote control 16 and comprises a first remote switch 17, a second remote switch 18, a third remote switch 19, and a fourth remote switch 20 operatively connected to microprocessor 408 of control unit 300 (FIG. 4). Remote switches 17, 18 and 19 functionally correspond to forward button 46, reverse button 48, and vacuum button 50 of handpiece 40 of FIG. 1. A fourth remote switch 20 is provided to expand the number of functions that may be performed by surgical biopsy system 10, but is not utilized in the embodiment of the present invention described herein. In this embodiment remote switches 17, 18, 19, and 20 are momentary switches that are normally open.

Still referring to FIG. 6, a device identifier 26 is provided on second circuit 214 and comprises conductors for providing a feedback signal to control unit 300. The control method logic of microprocessor 408 proceeds according to the device identifier 26 signal. Device identifier 26 tells microprocessor 408 if remote control 16 is physically plugged in to control unit 300 and, in one embodiment of the present invention, the presence of device identifier 26 renders buttons 46, 48, and 50 of handpiece 40 inoperable. Instructions to the operator as indicated on display 334 take into account whether the operator is using handpiece 40 or remote control 16 to operate the surgical biopsy system 10, and the graphics/instructions of display 334 are changed accordingly. When an operator chooses to use remote control 16 with handpiece buttons 46, 48 and 50 inoperable, handpiece 40 may be used without concern for inadvertently pressing buttons 46, 48, and 50 during the procedure and engaging an undesired function.

Figure 7:
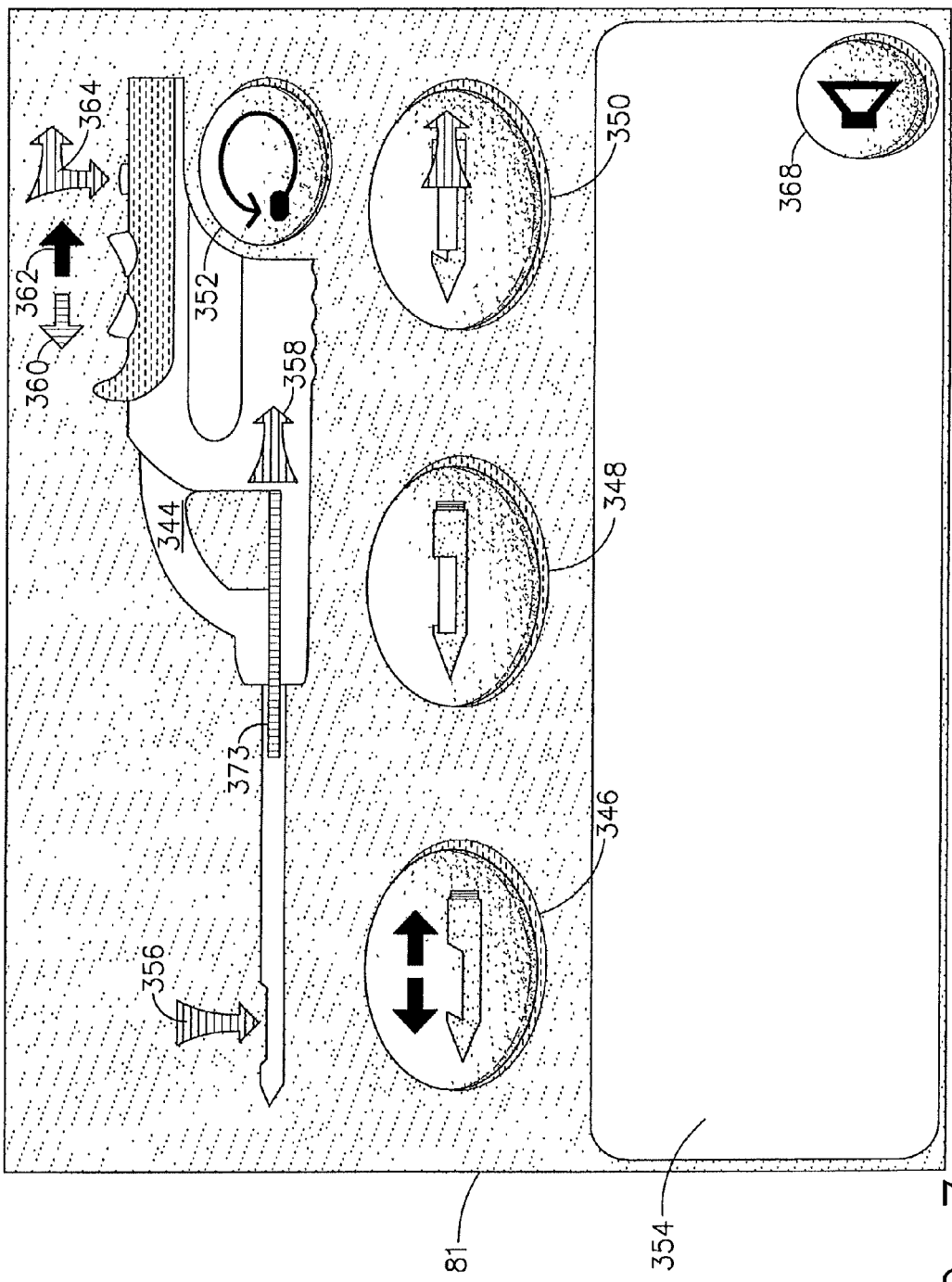
FIG. 7 is an illustration of one screen image on the display of the control unit shown in FIG. 3 wherein a number of operational modes are represented by icons.

In one embodiment of the present invention, three separate operational modes are available to the operator: a Positioning Mode, a Sampling Mode, and a Clear Probe Mode. FIG. 7 shows a screen image 81 of display 334 on which a control for each operational mode is displayed graphically in the form of icons, which icons may be associated with touchscreen controls. By pressing touch screen 336 in the region of the icon or otherwise selecting an icon as described herein, the icon selected becomes highlighted by a color change or other visual indication accompanied by a distinct audible beep from annunciator 332.

Screen image 81 is one of a plurality of images that appear on display 334 during the operation of surgical biopsy system 10. Screen image 81 includes a positioning control icon 346, a sampling control icon 348, and a clear probe control icon 350, which are positioned above a message window 354. Screen image 81 also includes a handpiece icon 344 with a cutter position indicator 373 to indicate the real-time position of cutter 96. A lateral vacuum indicator 356, an axial vacuum indicator 358, a forward control indicator 360, a reverse control indicator 362, and a vacuum control indicator 364 each become visually highlighted whenever activated by, for example, depressing a button on handpiece 40 or remote control device 16. Screen image 81 also includes an exit icon 352, which may be selected by an operator to exit the screen image 81. In one application, when exit icon 352 is selected, a new options screen is displayed with the following four options: use a new probe assembly, use a new holster, return to the procedure, and change settings. A volume control icon 368 is provided for setting the volume of the audible signals from control unit 300.

Figure 8:
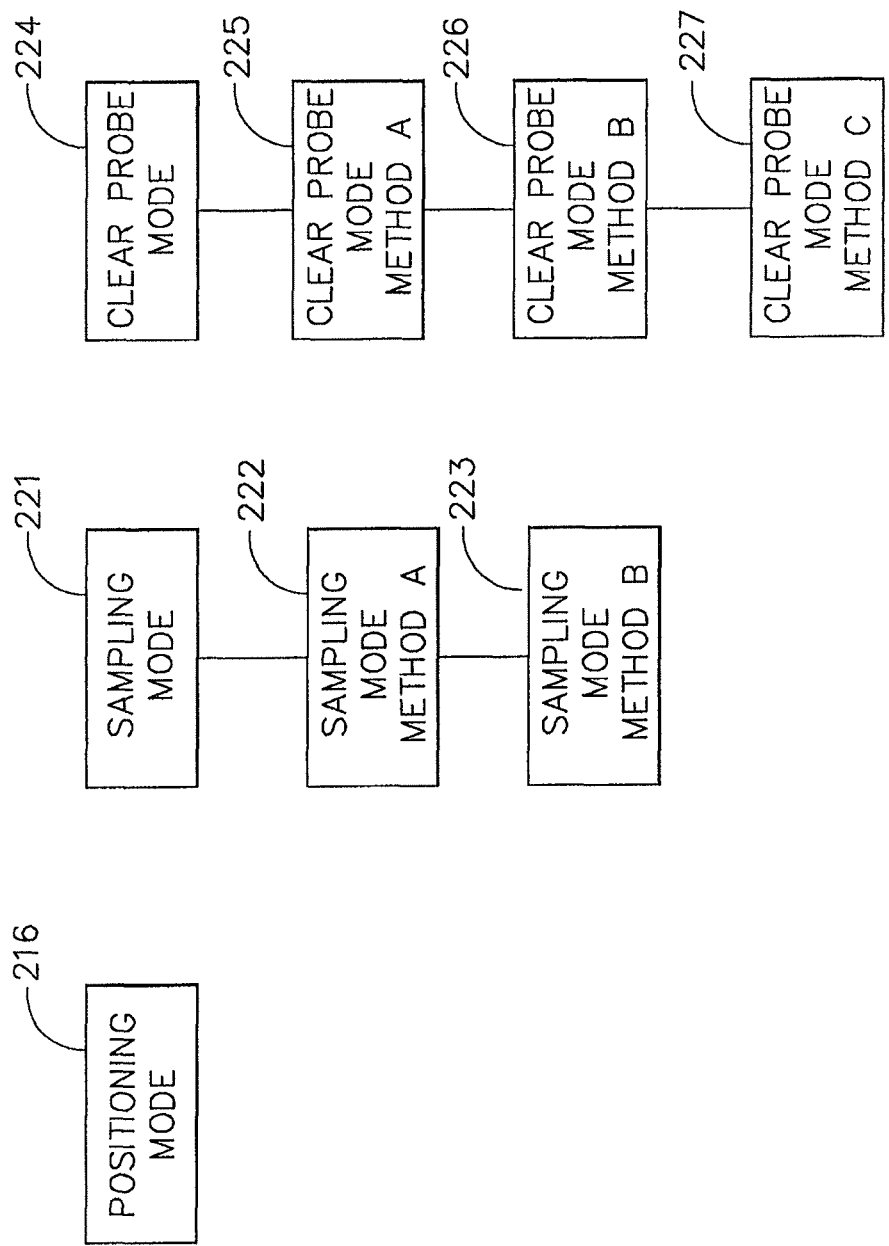
FIG. 8 is a schematic diagram wherein each block is representative of one operational mode or method of implementing a particular operational mode.

During a biopsy procedure, each mode of operation represented by icons 346, 348 and 350 is used for a particular portion of the general biopsy procedure. FIG. 8 includes blocks 216, 221 and 224 each of which are representative of a mode of operation which may be initiated by selecting one of icons 346, 348 or 350. Each of the selectable modes of operation are described in greater detail with respect to the flowcharts in FIGS. 9-13. The flowcharts illustrated in FIGS. 9-13 will be described with reference to forward button 46, reverse button 48 and vacuum button 50 of handpiece 40, however, it will be apparent to one of skill in the art that the modes of operation illustrated in FIGS. 9-13 will work with functionally corresponding switches of remote control 16. In particular, first remote switch 17, second remote switch 18, and third remote switch 19 may functionally correspond to forward button 46, reverse button 48 and vacuum button 50.

Referring to FIG. 8, block 216 represents the Positioning Mode: When in the Positioning Mode, the operator can accomplish preparatory tasks such as priming or flushing fluid collection system 22, verifying that port 78 is oriented adjacent to the tissue mass to be sampled, or injecting anesthetic fluid into tissue through port 78. In the Positioning Mode, the operator may translate cutter 96 axially in either direction. Normally cutter 96 does not rotate when being translated in the Positioning Mode. In the Positioning Mode, depressing forward button 46 moves cutter 96 distally until forward button 46 is released or until Position 4 is reached. Depressing reverse button 48 moves cutter 96 proximally until reverse button 48 is released or until Position 1 is reached. Depressing vacuum button 50 connects port 78 to lateral vacuum line 30 and axial vacuum line 32 until vacuum button 50 is released. With vacuum button 50 depressed, fluid flows from port 78 through lateral vacuum line 30 and from cutter 96 through axial vacuum line 32 to fluid collection system 22.

Upon completion of the preparatory or intervention task in the Positioning Mode, the operator may select the Sampling Mode of operation which is represented by block 221 in FIG. 8. When the system is in the Sampling Mode of operation, probe assembly 42 is programmed to automatically obtain tissue samples from the patient using one of two methods. The method used depends on an election by the operator during an operator's preference selection procedure that is completed before the Sampling Mode is selected. In the Sampling Mode, cutter translation speed, cutter rotation speed and actuation of fluid collection system 22 are preprogrammed and are controlled by feedback signals indicating the position of cutter blade 97. In the present embodiment, two sampling methods are available to the operator: Sampling Method A, which is represented by block 222 in FIG. 8; and Sampling Method B, which is represented by block 223 in FIG. 8. For either method, the operator presses and holds forward button 46 as cutter 96 moves from Position 1 to Position 2. This deliberate action insures that the operator is intentionally advancing cutter 96 while cutter blade 97 is exposed as it moves across collection surface 41. If Sampling Method A was selected during the preference selection procedure, pressing forward button 46 once moves cutter 96 from Position 2 to Position 4 severing a tissue sample in port 78 and stops cutter 96 at Position 4. Then when reverse button 48 is pressed once, cutter 96 moves from Position 4 to Position 1 and the severed tissue sample is deposited onto collection surface 41. If Sampling Method B was selected during the preference selection procedure, pressing forward button 46 once, moves cutter 96 from Position 2 to Position 4, severing a tissue sample. Cutter 96 then pauses for a predetermined length of time (e.g. 2-6 seconds), and then moves from Position 4 to Position 1, depositing the severed tissue sample onto collection surface 41.

The Clear Probe Mode as represented by Block 224 in FIG. 8, may be used to automatically clear tissue and/or fluids from piercer tube 74, In one embodiment of the surgical system, the Clear Probe Mode may include three clear probe methods, A, B, or C, which are selected by an operator during the preference selection procedure prior to entering Clear Probe Mode. Once the system is in the Clear Probe Mode, the operator presses and holds forward button 46 as cutter 96 advances from Position 1 to Position 2. In the Clear Probe Method A 225, an operator presses forward button 46 and cutter 96 advances to Position 3, axial vacuum line 32 pulses automatically, and cutter 96 returns to Position 1. For Clear Probe Method B as represented by block 226, the operator presses the forward button 46 and cutter 96 automatically moves to Position 4, axial vacuum line 32 pulses (opens and closes repeatedly), and then the cutter 96 returns to Position 1. For Clear Probe Method C as represented by block 227, the operator presses forward button 46 and cutter 96 automatically moves to Position 3, axial vacuum line 32 is pulsed, cutter 96 moves to Position 4, axial vacuum line 32 is pulsed again, and cutter 96 returns to Position 1. Upon completion of one of clear probe methods A, B, or C, the operator may select any mode including the Sampling Mode which is represented by block 221.

Figure 9A:
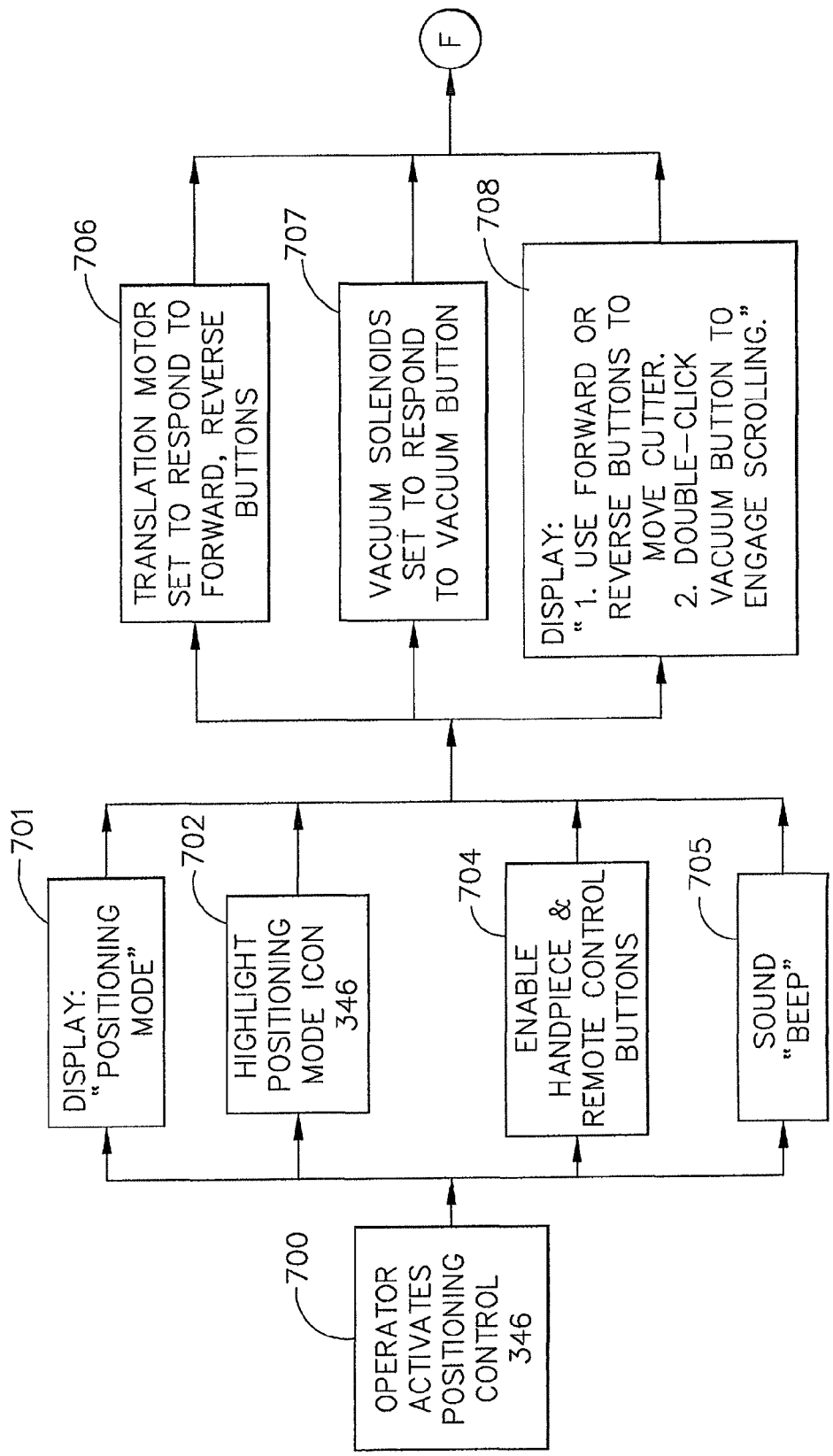
FIGS. 9A and 9B include flowcharts illustrating the steps in one embodiment of a particular mode of operation.
Figure 9B:
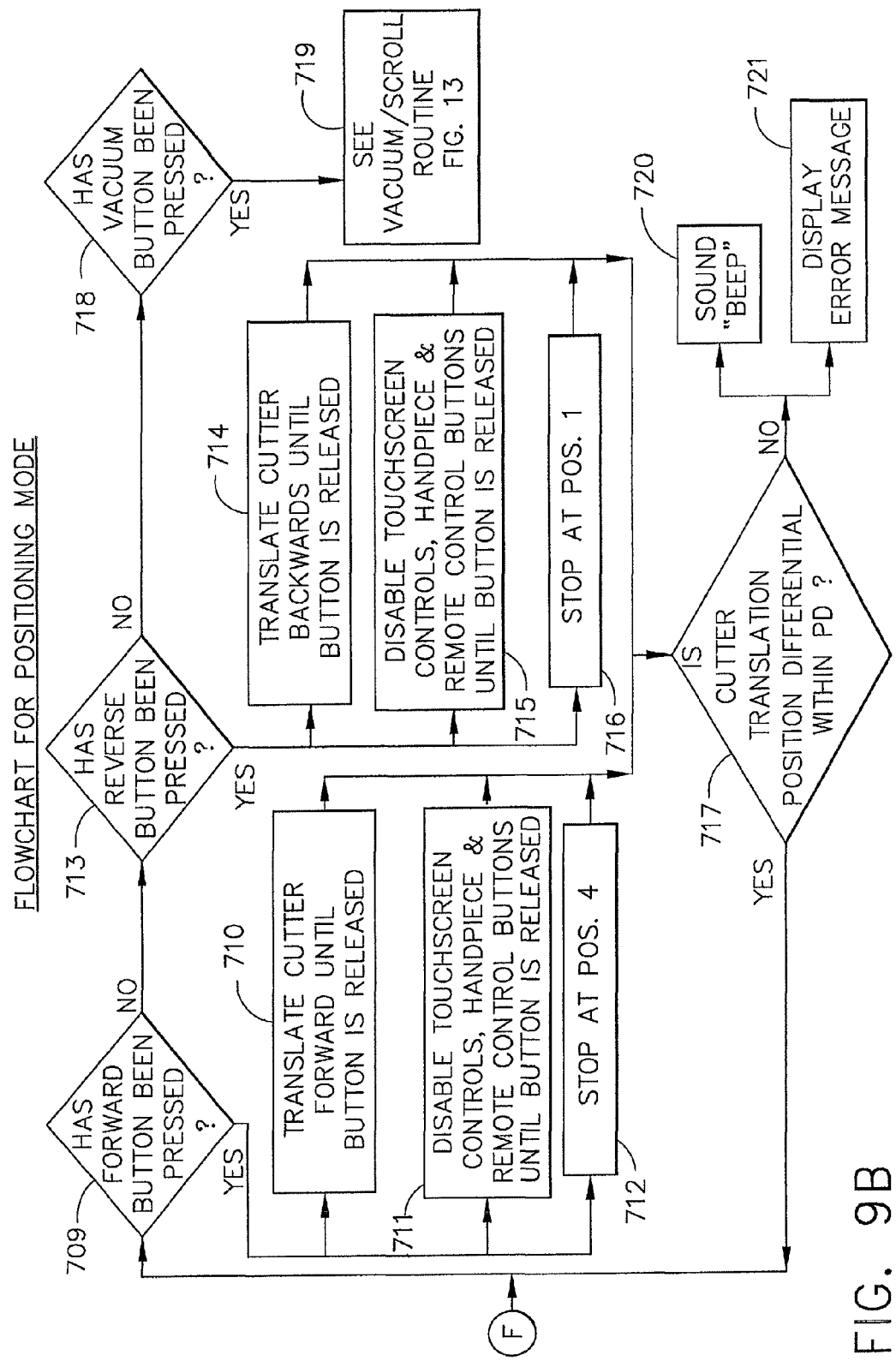

FIGS. 9A and 9B include flowcharts illustrating the steps in one embodiment of a Positioning Mode of operation. The flowchart in FIGS. 9A and 9B is divided in two parts at circles containing like letters. The flowcharts in FIGS. 9A and 9B illustrate one example of the interaction between an operator and control unit 300 with the system in the Position Mode of operation. In one embodiment of the present invention, the system starts in the Position Mode when screen image 81 comes up and it is not necessary to select position control icon 346. If, however, the system is not in the Position Mode, position control icon 346 may be selected by the surgeon using the procedure described herein with reference to FIG. 13. In step 700 of FIG. 9A, when position control icon 346 is selected or screen image 81, display 334 displays "POSITIONING MODE" in message window 354 (step 701), positioning control icon 346 is highlighted (step 702), forward button 46, reverse button 48, and vacuum button 50 are enabled (step 704) and control unit 300 sounds a distinct "beep" (step 705). In step 706 power transmission source 24 is set to respond to the forward button 46 and reverse button 48. In step 707 the vacuum solenoids, 23 and 25, are set to respond to vacuum button 50. In step 708 display 334 shows the message "1. USE FORWARD OR REVERSE BUTTONS TO MOVE CUTTER. 2. DOUBLE-CLICK VACUUM BUTTON TO ENGAGE SCROLLING." Continuing the flowchart logic in FIG. 9B, in steps 709, 713 and 718 control unit 300 queries handpiece 40 to see if forward button 46 has been pressed, if the reverse button 48 has been pressed, or if the vacuum button 50 has been pressed. If the operator pressed the forward button 46 in step 709 then in step 710 cutter 96 translates forward until forward button 46 is released. In step 711, the touchscreen controls, handpiece buttons 46 and 50 or remote control switches 17, 18 and 19 are disabled until forward button 46 is released. In step 712 cutter 96 automatically stops at Position 4. If the reverse button 48 was pressed in step 713 then in step 714 cutter 96 translates proximally (backwards) until the operator releases reverse button 48 or cutter 96 stops at Position 1 in step 716. In Step 715 the touchscreen controls, handpiece buttons 46, 48 and 50, and remote control switches 17, 18 and 19 are disabled until reverse button 48 is released.

Translation of cutter 96 is measured in step 717: If cutter translation position differential is less than predetermined value PD then the positioning control mode continues to step 709. If not, control unit 300 sounds a distinct "beep" in step 720 and displays an error message in step 721.

FIGS. 10A, 10B, 10C, 10D, and 10E include a flowchart illustrating the steps in one embodiment of a Sampling Mode of operation, The flowchart in FIGS. 10A, 10B, 10C, 10D and 10E is divided into five parts at circles containing like letters. The flowcharts in FIGS. 10A, 10B, 10C, 10D and 10E illustrate one example of the interaction between the operator and control unit 300 with the system in the Sampling Mode of operation. As illustrated in step 600 of FIG. 10A, when sampling control icon 348 is selected on screen image 81 the Sampling Control Mode of operation is initiated. In step 601 handpiece buttons 46, 48 and 50 and remote control switches 17, 18 and 19 are disabled. In step 602 sampling control icon 348 on screen image 81 is highlighted. In step 603 display 334 shows "SAMPLING MODE" in message window 354, and in step 604 control unit 300 sounds a distinct "beep". Next, in step 605, cutter 96 translates to Position 1. Translation of cutter 96 is monitored in step 606 and, if position differential is not within PD, control unit 300 sounds a "beep" and displays an error message in step 607. In step 608 touchscreen controls, handpiece buttons 46, 48 and 50, and remote control switches 17, 18 and 19 are enabled. Otherwise, Sampling Control Mode continues. In step 609 forward button 46 and vacuum button 50 are enabled, touchscreen controls are also enabled in step 610, and in step 611 display 334 shows "1. USE FORWARD BUTTON TO TAKE SAMPLE. 2. USE ANY BUTTON TO ABORT. 3. DOUBLE-CLICK VACUUM BUTTON TO ENGAGE SCROLLING."

When the operator presses the forward button with the system in the Sampling Mode, it is detected in step 612. In step 613, the operator has the option of double-clicking the vacuum button to enter a vacuum/scroll routine (to be described with reference to FIG. 13) in order to select a different operational mode, such as Positioning Mode or Clear Probe Mode. If the operator selects the forward button, the system stays in the Sampling Mode and in step 615 touchscreen controls are disabled, in step 616 a "beep" is sounded, and in step 617 the "smart vac" routine (to be described with reference to FIG. 12) is ended if it had been previously engaged. In step 618, the operator presses and holds forward button 46 until cutter 96 reaches Position 2. In step 619, if the button is released early a message "PRESS AND HOLD FORWARD BUTTON" is displayed to remind the operator to hold forward button 46 down until Position 2 is reached. In step 620, cutter 96 continues to translate to Position 4. In step 621 lateral vacuum line 30 and axial vacuum line 32 are opened automatically to connect fluid canister 318 to handpiece 40. As illustrated in step 622, forward button 46, reverse button 48, and vacuum button 50 are enabled to abort (stop cutter translation and rotation) the Sampling Mode by pressing any one of them once. In step 623, cutter rotation speed is accelerated to Q before reaching Position 3. A preferred value of Q is 1100 revolutions per minute, although this value may vary depending upon the requirements of the system.

Figure 10A:
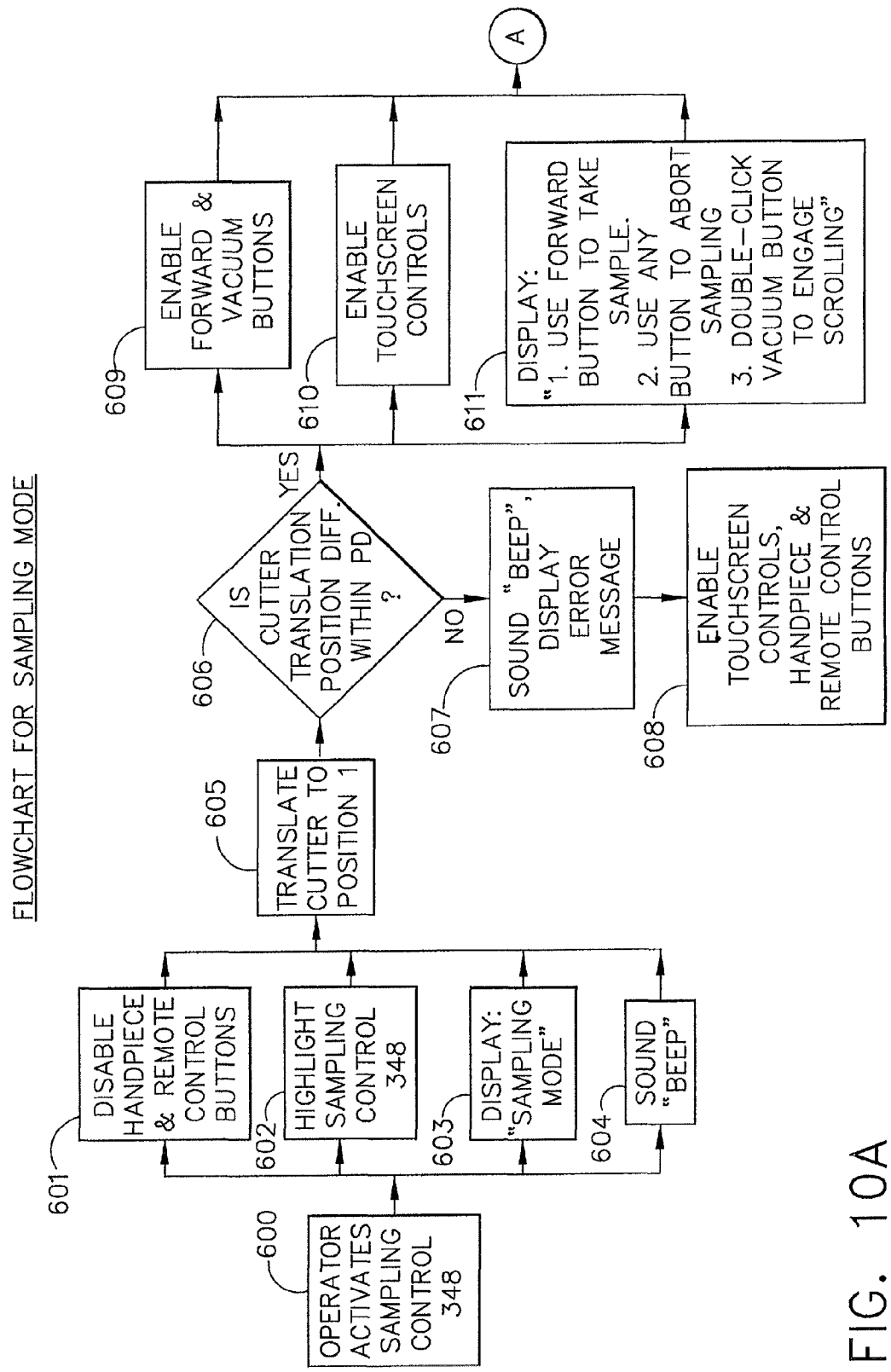
FIGS. 10A, 10B, 10C, 10D, and 10E include flowcharts illustrating the steps in one embodiment of a further mode of operation.
Figure 10B:
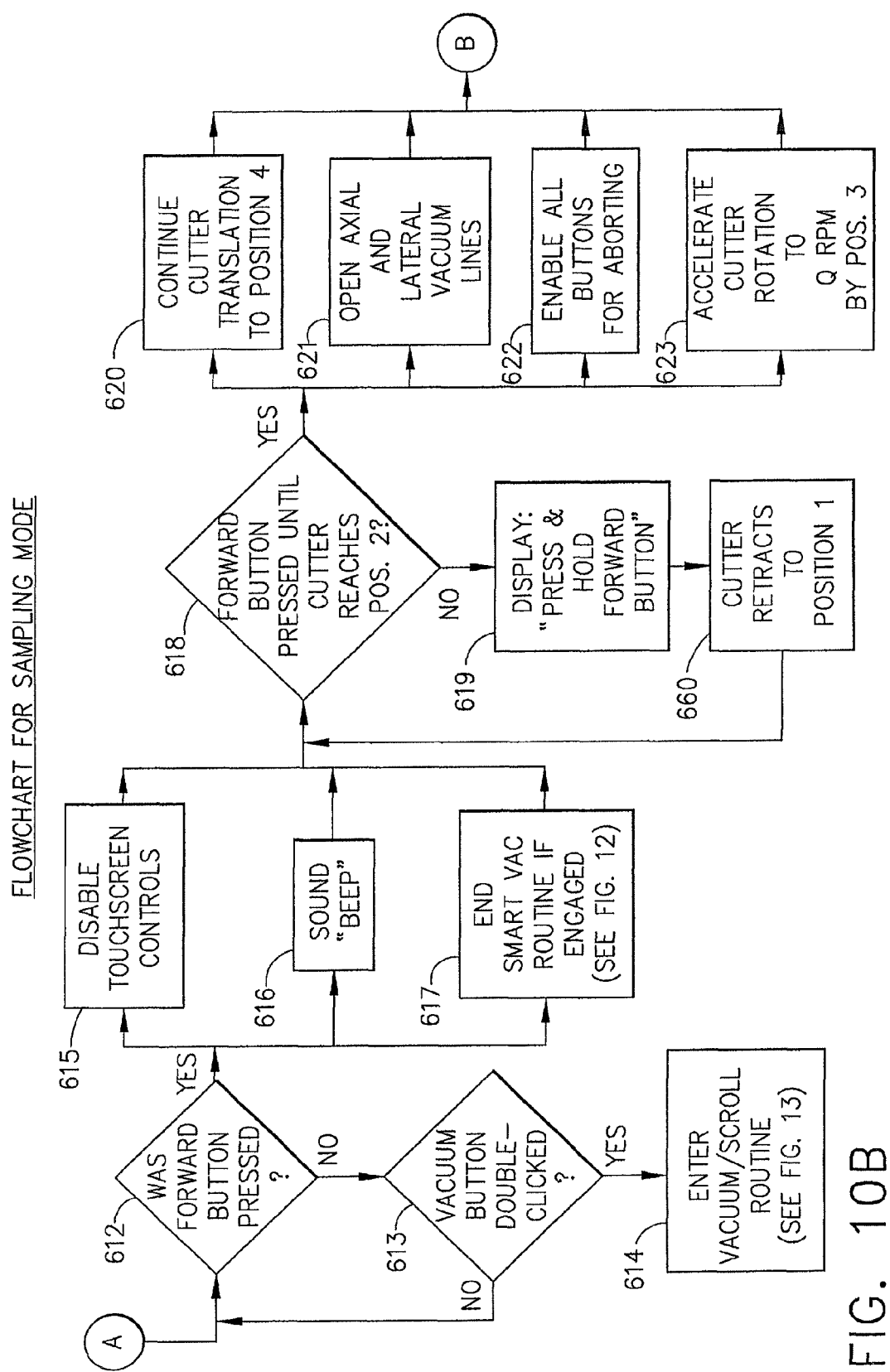
Figure 10C:
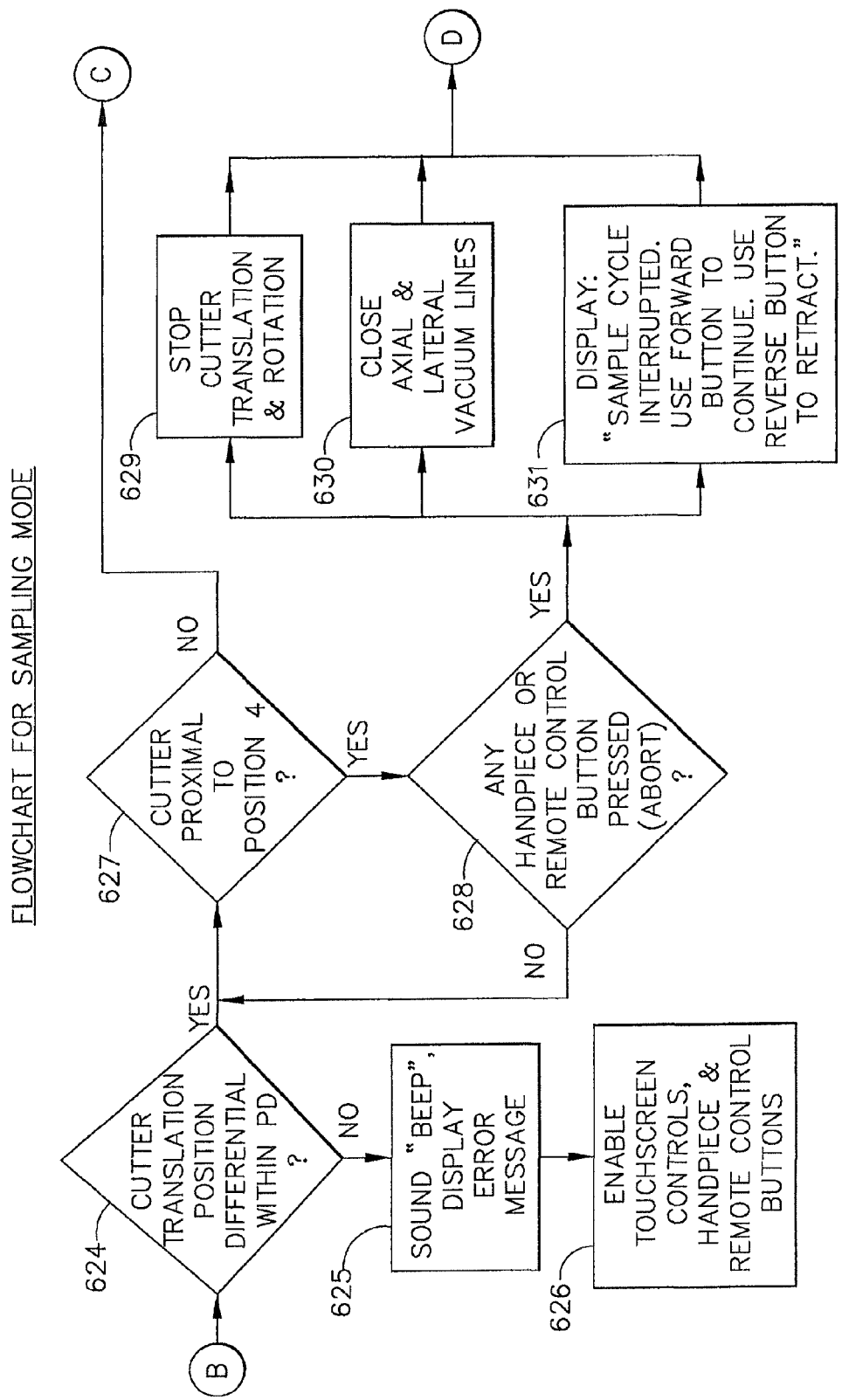

In step 624 of FIG. 10C, cutter translation position is again compared to PD. If the actual cutter position differential is not within PD, control unit 300 sounds a "beep" and displays an error message in step 625 and the controls and buttons are enabled in step 626. If cutter 96 is translating properly and is proximal to Position 4, cutter 96 continues to translate distally unless any button on handpiece 40 or on remote control 16 is pressed to abort the sampling mode step 628. Once cutter 96 reaches Position 4, the Sampling Mode proceeds in accordance with the flowchart illustrated in FIG. 10D. If the Sampling Mode is aborted at step 628, cutter translation and rotation is stopped in Step 629, and both lateral and axial vacuum lines, 30 and 32, are closed in step 630. Display 334 then reads "SAMPLE CYCLE INTERRUPTED. USE FORWARD BUTTON TO CONTINUE. USE REVERSE BUTTON TO RETRACT." in step 631.

Figure 10D:
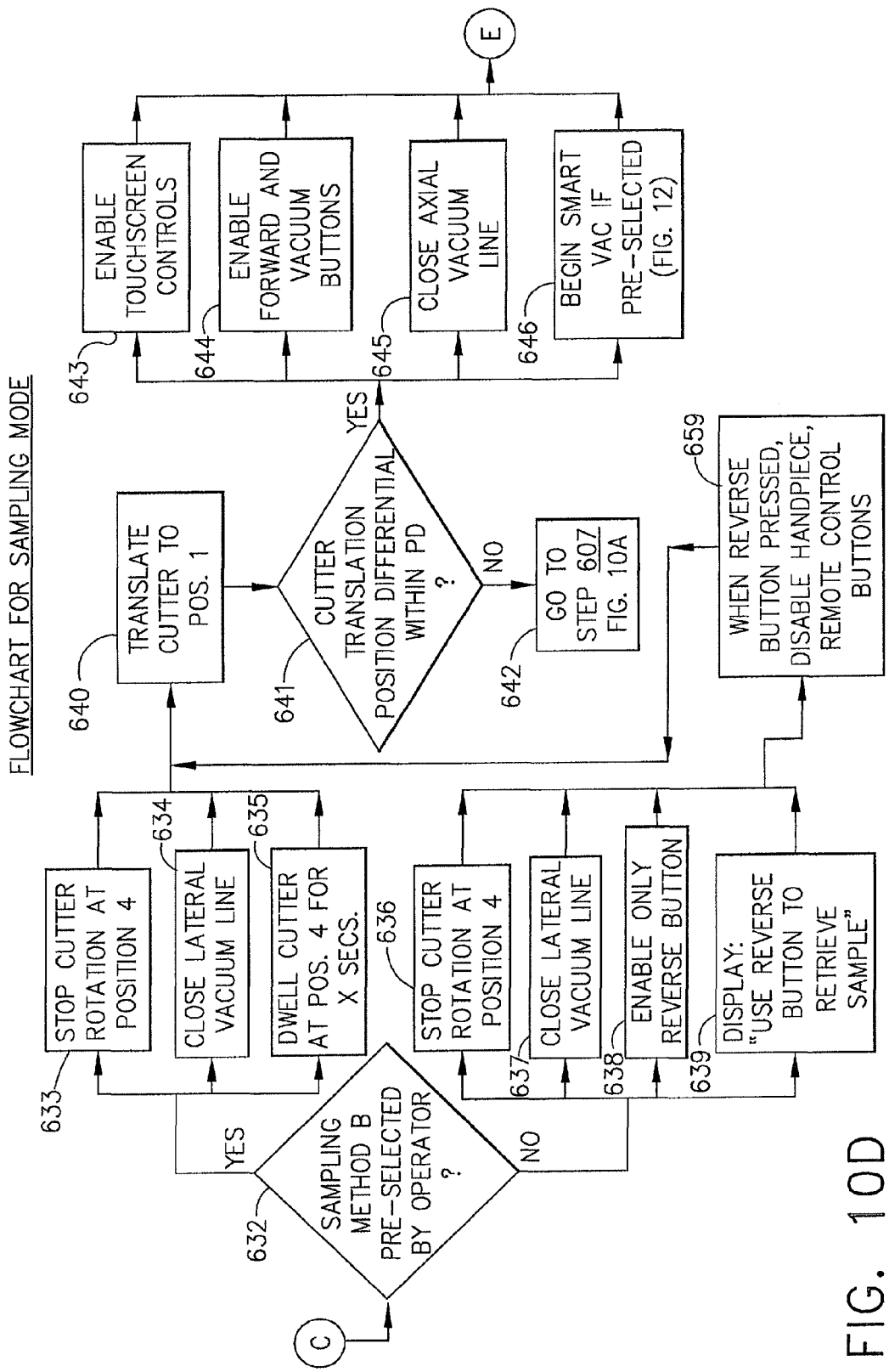
Figure 12:
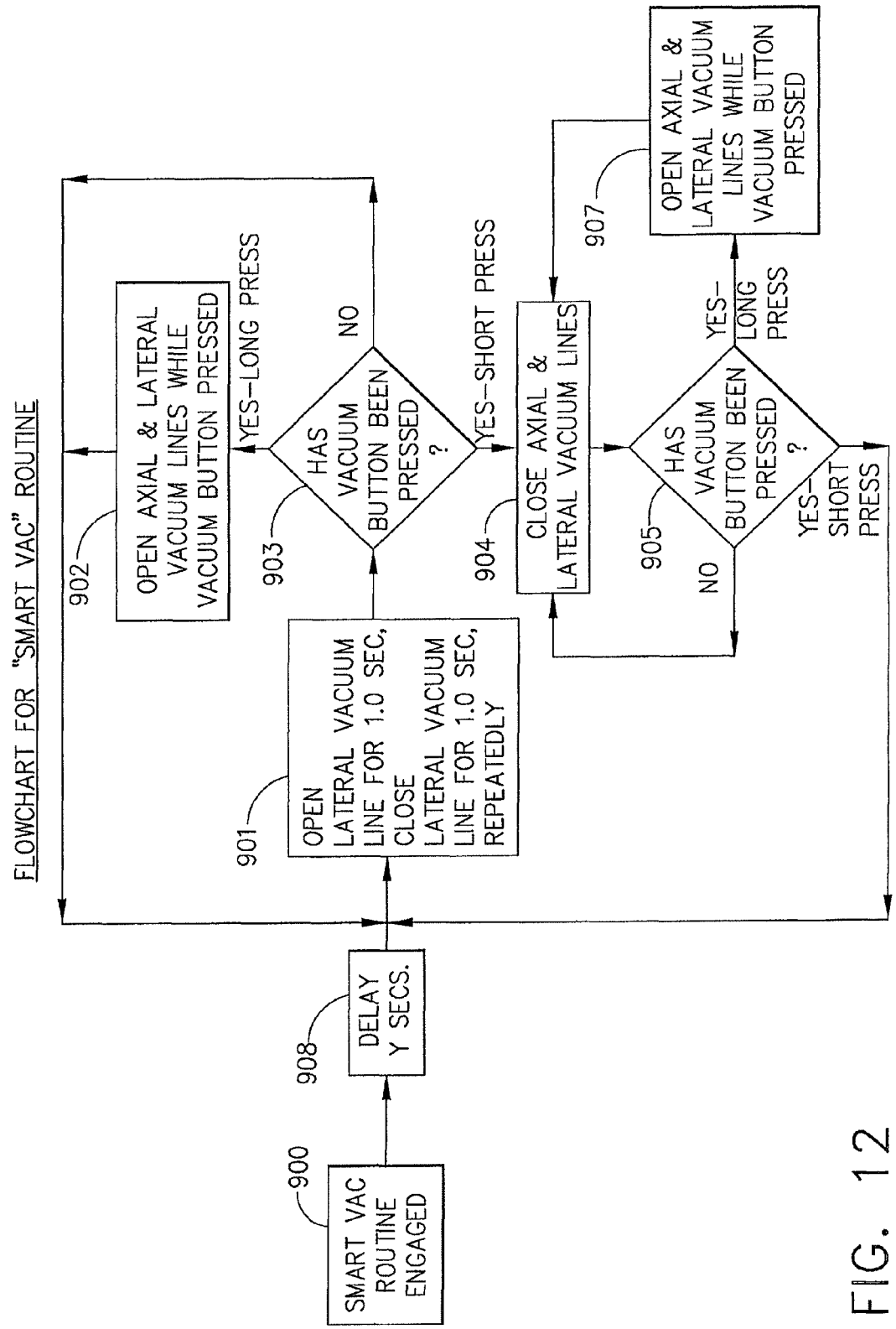
FIG. 12 is a flowchart illustrating the steps of a "smart vac" routine.

In FIG. 10D the system is in the Sampling Mode and cutter 96 is translating towards Position 4 at a predetermined translation speed. In step 632 the Sampling Mode continues according to which of the two sampling mode methods, A or B, was pre-selected by the operator during the preference selection routine. If Sampling Method B was selected, then cutter rotation is stopped at Position 4 step 633, lateral vacuum line 30 is closed step 634, and cutter 96 dwells at Position 4 for X seconds 635. A preferred value for X is approximately in the range of 2 to 6 seconds. Cutter 96 then automatically translates back to Position 1. If Sampling Method A was pre-selected by the operator, cutter rotation is stopped at Position 4 in step 636 and lateral vacuum line 30 is closed in step 637. The reverse button 48 is enabled in step 638 and display 334 reads "USE REVERSE BUTTON TO RETRIEVE SAMPLE." in step 639. When the reverse button is pressed in step 659, the buttons on handpiece 40 and on remote control 16 are disabled. Cutter translation Position 1 begins in step 640. Cutter translation position is checked in step 641. If cutter translation position is not within PD in step 642, control unit 300 sounds a "beep" and an error message is displayed in step 607. If cutter translation position is OK, then cutter 96 translates to Position 1. When cutter 96 reaches Position 1, touchscreen controls 643 are enabled in step 643, forward button 46 and vacuum button 48 are enabled in step 644, axial vacuum 32 is closed in step 645, and the smart vac routine of FIG. 12 is begun if pre-selected during the preference selection routine in step 646.

Figure 10E:
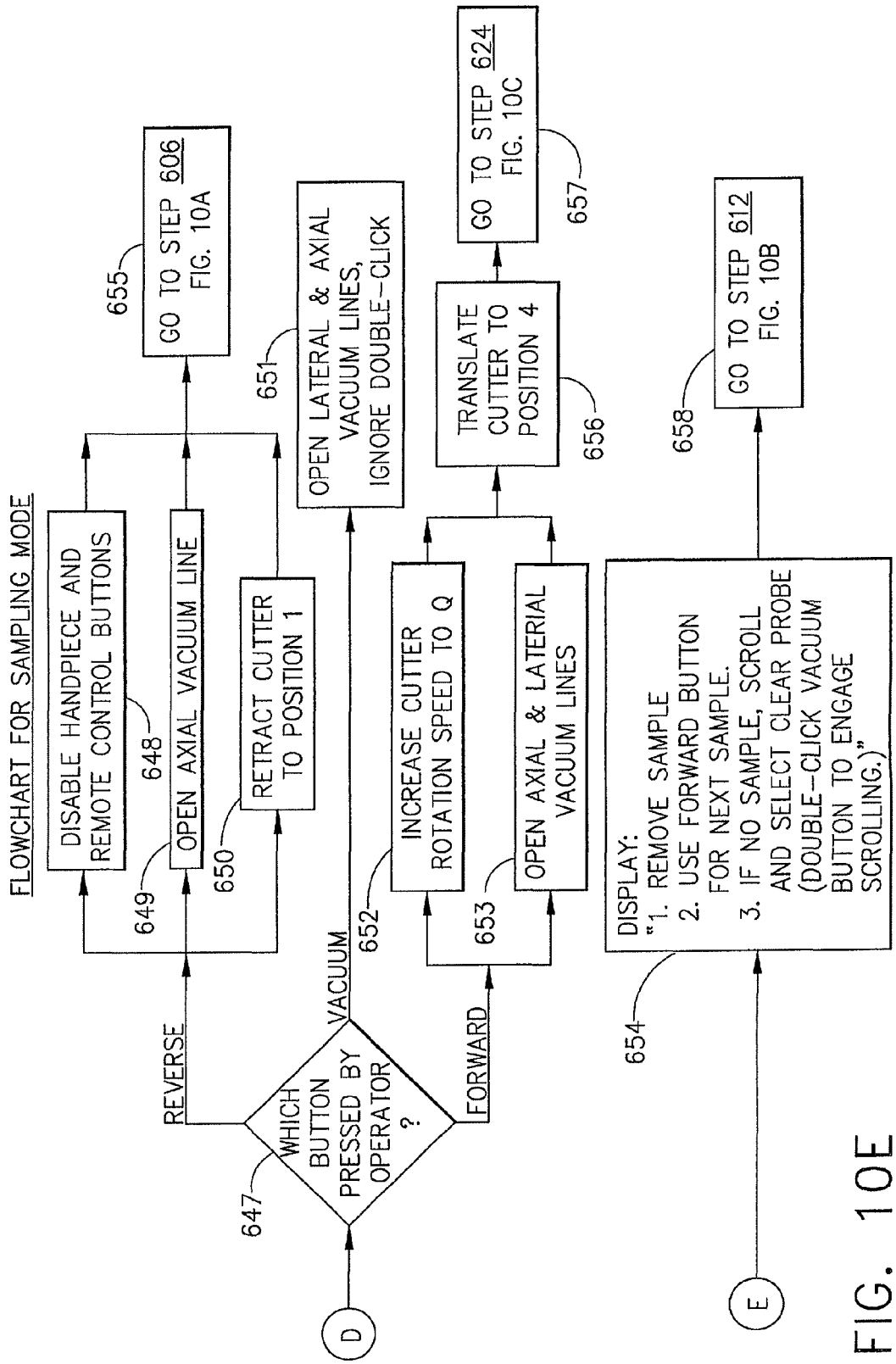

In FIG. 10E the Sampling Mode flowchart continues. In step 654 screen image 81 displays: "1. REMOVE SAMPLE. 2. USE FORWARD BUTTON FOR NEXT SAMPLE. 3. IF NO SAMPLE, SCROLL AND SELECT CLEAR PROBE (DOUBLE-CLICK VACUUM BUTTON TO ENGAGE SCROLLING.)" The Sampling Mode flowchart resumes at step 612 of FIG. 10B, where control unit 300 queries handpiece 40 to see if the forward button 48 is depressed. If the Sampling Mode was aborted as described in steps 628-631 of FIG. 10C, then the sampling mode logic proceeds to step 647 in FIG. 10E. In step 647 control unit 300 determines which button was pushed after the Sampling Mode was aborted. If reverse button 48 was pressed, then in step 648 all buttons on handpiece 40 are disabled axial vacuum line 32 is opened in step 649, and cutter 96 is retracted to Position 1 in step 650. In step 655 the Sampling Mode moves back to step 606 of FIG. 10A to check positional difference. If in step 647 vacuum button 50 is pressed, then in step 651 both lateral vacuum line 30 and axial vacuum line 32 are opened and control unit 300 ignores a double-click. If in steps 647 forward button 46 was pressed, then in step 652, cutter rotation is increased to speed Q and lateral and axial vacuum lines are opened again in step 653. Cutter 96 then translates to Position 4 in step 656. In step 657, cutter translation position is checked again as described for step 624 of FIG. 10C.

Figure 11A:
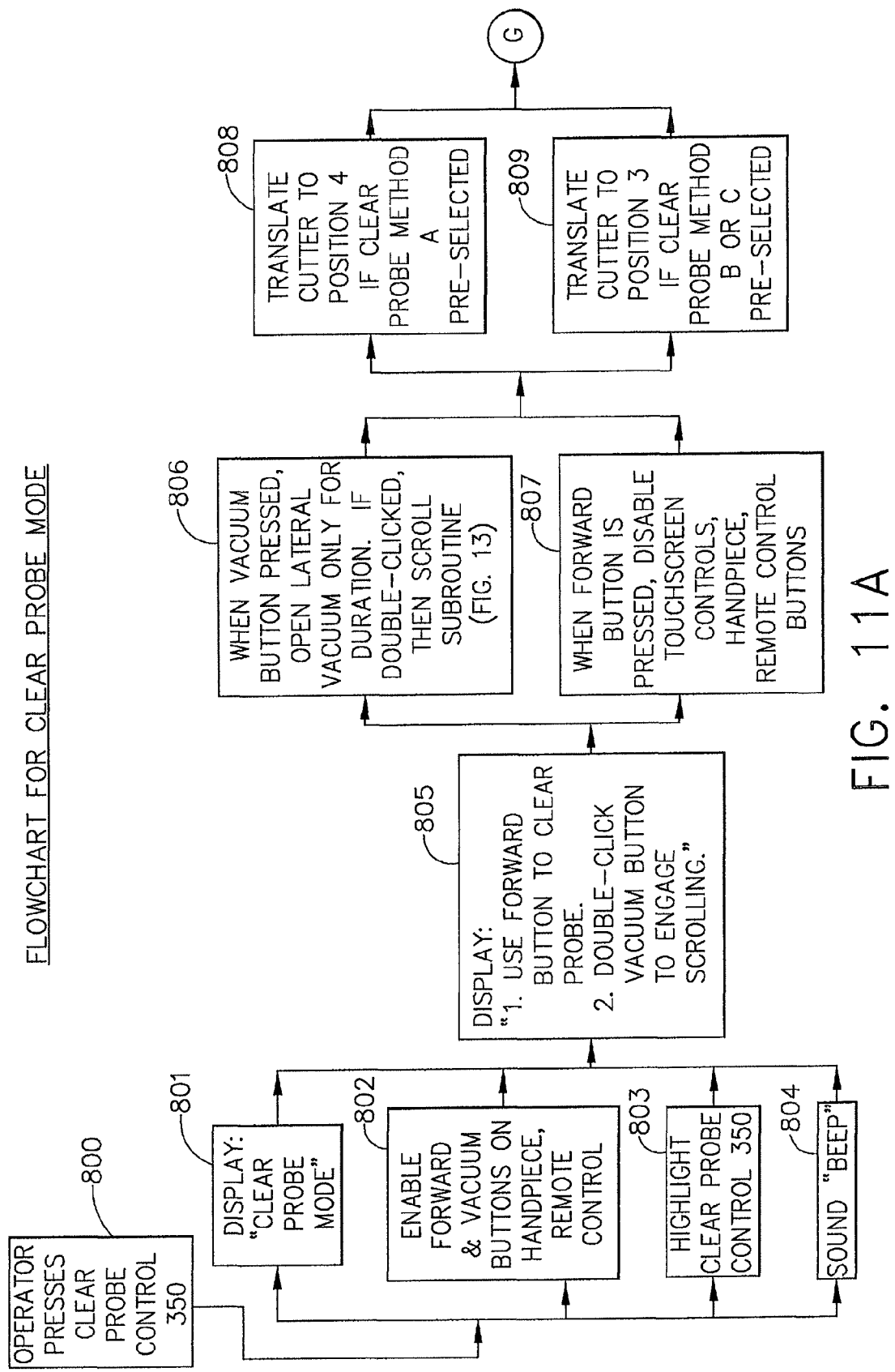
FIGS. 11A and 11B include flowcharts illustrating the steps in one embodiment of a further mode of operation.
Figure 11B:
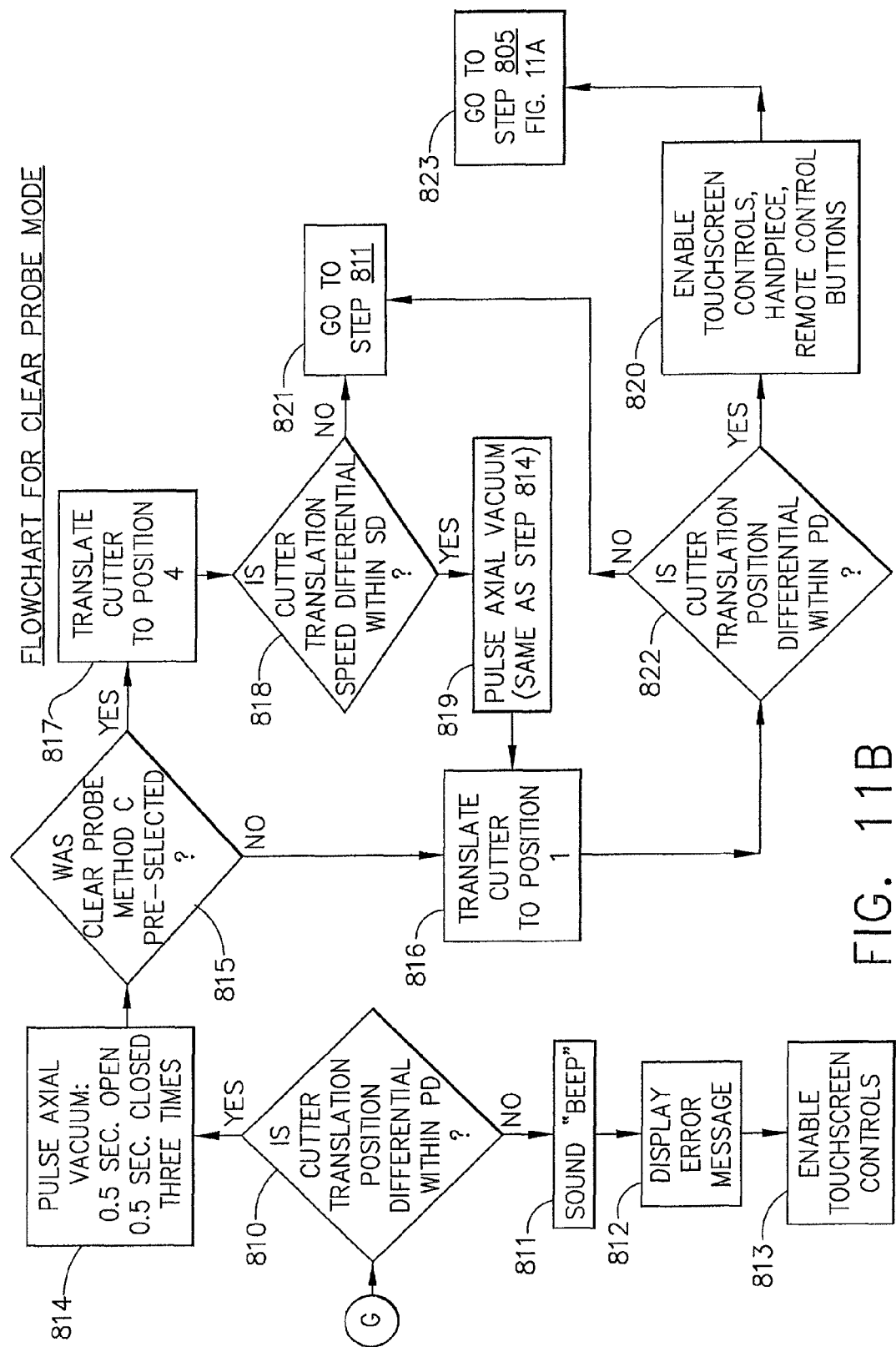

FIGS. 11A and 11B include a flowchart illustrating the steps in one embodiment of a Clear Probe Mode of operation. The flowchart in FIGS. 11A and 11B is divided in two parts at circles containing like letters. The flowcharts in FIGS. 11A and 11B illustrate the Clear Probe Mode of operation. As illustrated in step 801 of FIG. 11A, when clear probe control icon 350 is selected, the Clear Probe Mode of operation is initiated and display 334 displays "CLEAR PROBE MODE" in message window 354. In step 802, forward button 46 and vacuum button 50 are enabled, in step 802 the Clear Probe Mode is highlighted and control unit 300 sounds a distinct "beep" in step 804. In step 805, control unit 300 displays "1. USE FORWARD BUTTON TO CLEAR PROBE. 2. DOUBLE-CLICK VACUUM BUTTON TO ENGAGE SCROLLING." If the operator presses and holds vacuum button 50 in step 806, lateral vacuum line 30 is opened until vacuum button 50 is released. If the operator double-clicks on vacuum button 50, then the vacuum/scroll routine of FIG. 13 begins. If the operator presses forward button 46, then all controls and buttons are disabled in step 807. If Clear Probe Method A had been pre-selected, in step 808 cutter 96 translates to Position 4. If the Clear Probe Methods B or C had been selected, cutter 96 translates to Position 3 in step 809.

The flowchart illustrating the Clear Probe Mode of operation continues in FIG. 11B at step 810 where cutter translation position is again checked. If the cutter translation position differential is not within PD as before, then a "beep" is sounded in step 811, an error message is displayed in step 812 and the controls are enabled in step 813. If the differential is within PD, then, in step 814, the axial vacuum line 32 is "pulsed" by opening it to fluid collection system 22 for 0.5 seconds, closing it for 0.5 seconds, and repeating the sequence two more times. Next, in step 815, control unit 300 determines whether Clear Probe Method C had been pre-selected by the operator. If not, then cutter 96 translates to Position 1, per step 816, with the axial vacuum on during translation. If Clear Probe Method C has been selected, then, in step 817, cutter 96 translates to Position 4. Then in step 818 cutter translation position differential is checked, and, if it is within PD, axial vacuum line 32 is pulsed again in step 819. If the position differential is not within PD, then, in step 821, the flowchart goes to step 811. After pulsing axial vacuum line 32 in step 819, cutter 96 translates to Position 1, with axial vacuum on during translation, in step 816. Again as cutter 96 translates to Position 1, in step 822 the cutter translation position differential is checked to be sure it is within PD. If the differential is within PD, all controls and buttons are enabled and the Clear Probe Mode of operation proceeds to step 805 of FIG. 11A so that the mode may either be repeated or scrolled to an alternate mode of operation (positioning or sampling).

FIG. 12 is a flowchart illustrating a smart vac routine for dislodging tissue that may be stuck in port 78. If the operator pre-selected the smart vac routine during the operator's preference selection the smart vac routine engages automatically, at Position 1, after a first sample has been removed, in the Sampling Mode of operation Once control unit 300 engages the smart vac routine in step 900, there is a momentary delay of Y seconds in order to allow time for the operator to remove the tissue sample from collection surface 41 in step 908. A preferred value for Y is approximately eight seconds. Once the smart vac routine is initiated, then lateral vacuum line 30 is opened to the vacuum source for 1.0 seconds, closed for 1.0 seconds, and the process is repeated until the next sample is taken (see step 617, FIG. 10B), or until the vacuum button 50 is pressed. If the vacuum button is depressed for a long time (at least about 0.5 seconds) then in step 902 the axial and vacuum lines are opened. If vacuum button 50 was depressed and held, then when vacuum button 50 is released the smart vac routine then continues to pulse lateral vacuum line 30 in step 901. If vacuum button 50 was pressed quickly, then, in step 904, axial vacuum line 32 and lateral vacuum line 30 are closed. In step 905, the steps are repeated, short press of vacuum button 50 sends the smart vac routine to step 901 to pulse lateral vacuum line 30. A long press sends the smart vac routine to step 907 and step 907 opens the axial vacuum line 32 and lateral vacuum line 30 while vacuum button 50 is depressed. Then both lines are closed at step 904, when the button is released. If at step 905 the vacuum button was not pressed at all, the smart vac routine returns to step 904.

Figure 13:
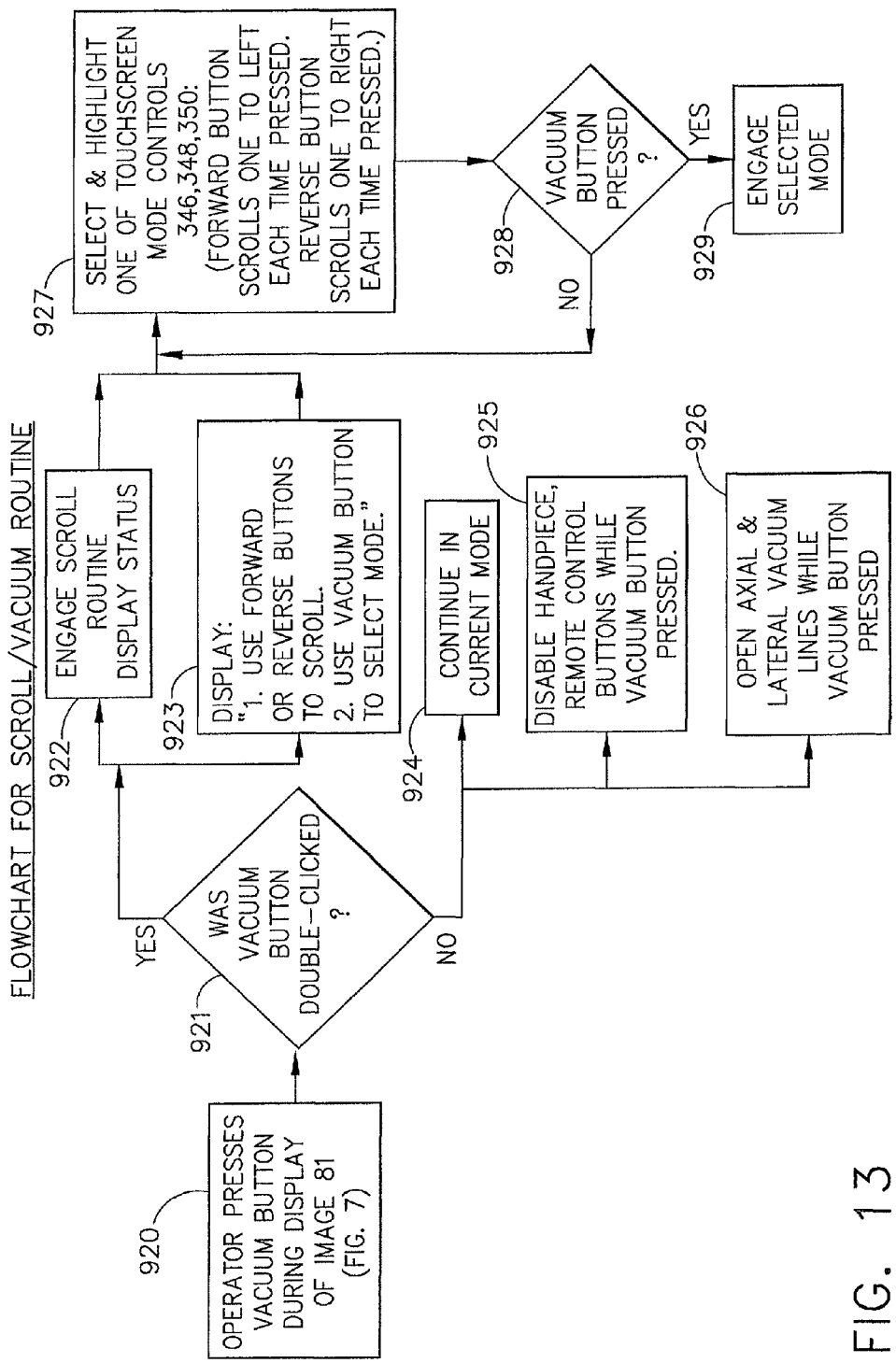
FIG. 13 is a flowchart illustrating the steps of a "vacuum/scroll" routine.

The scroll/vacuum routine is illustrated by a flowchart in FIG. 13. With screen image 81 displayed, the operator may use vacuum button 50 to set the system to scroll through the screen icons or to perform other tasks. If display 334 shows screen image 81, then in step 921 the operator may press vacuum button 50 once to, for example, open the axial vacuum line 32 and lateral vacuum line 30 until vacuum button 50 is released. While vacuum button 50 is depressed, the forward button 46 and reverse button 50 are disabled in step 925 and the current operational mode continues in step 924. If at step 921 the control unit 300 recognizes that the vacuum button had been double-clicked, then the scroll routine engages in step 922 and the status is displayed in steps 922, 923: "1. USE FORWARD OR REVERSE BUTTONS TO SCROLL. 2. USE VACUUM BUTTON TO SELECT MODE." In step 927 one of the touchscreen mode control icons (positioning control icon 346, sampling control icon 348, clear probe control 350 icon) may be selected by using either the forward button 46 (to scroll right to left one position each time forward button 46 is pressed) or the reverse button 48 (to scroll left to right one position each time reverse button 48 is pressed.) When the desired control icon is highlighted, the operator presses the vacuum button to enable the selected mode in steps 928 and 929. Otherwise, the operator may continue to scroll through the controls as described in step 927.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims.

The invention claimed is:

1. A biopsy system comprising:
(a) a handpiece including an elongated, hollow piercer and a cutter rotatably and axially positionable relative to the piercer, the piercer having a lateral port for receiving a tissue sample into the piercer;
(b) a control unit operably associated with the handpiece for selecting from two or more operational modes once the control unit is powered on, wherein each of the two or more operational modes is operably associated with a speed of the cutter; and
(c) a display operably associated with the control unit, wherein the display is operable to show a first region and a second region, wherein the first region is visually distinguishable from the second region, wherein at least a portion of the first region represents the cutter.

2. The biopsy system of claim 1, wherein the speed of the cutter comprises a rotational speed associated with the cutter.

3. The biopsy system of claim 1, wherein at least one of the first region or the second region represents a position of the cutter.

4. The biopsy system of claim 3, wherein the at least one of the first region or the second region further represents a realtime position of the cutter.

5. The biopsy system of claim 1, wherein the display further comprises an LCD display.

6. The biopsy system of claim 1, wherein the display is operably configured to display at least one selectable image.

7. The biopsy system of claim 1, wherein the speed of the cutter comprises a translation speed associated with the cutter.

8. The biopsy system of claim 1, wherein at least one of the two or more operational modes is operable for use with a high density mass of breast tissue of a patient.

9. The biopsy system of claim 1, wherein the display is further configured to display a handpiece image, wherein the handpiece image is associated with at least a portion of the handpiece.

10. The biopsy system of claim 1, wherein one of the two or more operational modes is operably associated with a first translational speed of the cutter, wherein another of the two or more operational modes is operably associated with a second translational speed of the cutter, wherein the first translational speed is different from the second translational speed.

11. The biopsy system of claim 1, wherein the display further comprises at least one textual message region, wherein the textual message region is configured to convey a textual message to the user.

12. The biopsy system of claim 1, wherein the display is operably configured to visually highlight at least one of the first region or the second region.

13. The biopsy system of claim 12, wherein the highlighting of the at least one of the first region or the second region is operably controlled by at least one button on the handpiece.

14. The biopsy system of claim 1, wherein the first region is configured to show the position of the cutter relative to the hollow piercer.

15. The biopsy system of claim 1, wherein the display further comprises a vacuum indicator.

16. A biopsy system comprising:
(a) a handpiece including an elongated, hollow piercer and a cutter rotatably and axially positionable relative to the piercer, the piercer having a lateral port for receiving a tissue sample into the piercer;
(b) a control unit operably associated with the handpiece for selecting from two or more operational modes once the control unit is powered on, wherein at least one of the two or more operational modes is operably associated with a preprogrammed sampling mode; and
(c) a display operably associated with the control unit, wherein the display is operable to show a first region and a second region, wherein the first region is configured to show a first aspect operably associated with the cutter, wherein the second region is configured to show a second aspect operably associated with the cutter.

17. The biopsy system of claim 16, wherein the sampling mode is associated with a rotational speed of the cutter, wherein the sampling mode is further with a translational speed of the cutter.

18. The biopsy system of claim 16, wherein the sampling mode is configured for use with a high density mass of breast tissue of a patient.

19. The biopsy system of claim 16, wherein the first region and the second region are associated with a realtime position of the cutter.

20. A biopsy system comprising:
(a) a handpiece including an elongated, hollow piercer and a cutter rotatably and axially positionable relative to the piercer, the piercer having a lateral port for receiving a tissue sample into the piercer;

(b) a control unit operably associated with the handpiece for selecting from two or more operational modes, wherein each of the two or more operational modes comprises at least one preprogrammed operation, wherein the at least one preprogrammed operation is configured to adjust a speed of the cutter in accordance with mechanical resistance encountered by the cutter; and (c) a user interface operably associated with the control unit, wherein the user interface is operable to display a first region and a second region, wherein the first region is visually distinguishable in relation to the second region, wherein the first region is operably associated with the cutter.

* * * * *